United States Patent
Brederlow et al.

(10) Patent No.: US 7,084,641 B2
(45) Date of Patent: Aug. 1, 2006

(54) MEASURING CELL AND MEASURING FIELD COMPRISING MEASURING CELLS OF THIS TYPE, USE OF A MEASURING AND USE OF A MEASURING FIELD

(75) Inventors: Ralf Brederlow, Munich (DE); Bjorn-Oliver Eversmann, Munich (DE); Ivo Koren, Munich (DE); Christian Paulus, Weilheim (DE); Roland Thewes, Grobenzell (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 10/754,909

(22) Filed: Jan. 9, 2004

(65) Prior Publication Data

US 2004/0207384 A1    Oct. 21, 2004

Related U.S. Application Data

(63) Continuation of application No. PCT/DE02/02526, filed on Jul. 10, 2002.

(30) Foreign Application Priority Data

Jul. 10, 2001    (DE)    ................ 101 33 363

(51) Int. Cl.
G01R 27/26    (2006.01)
G01N 27/00    (2006.01)
(52) U.S. Cl. .............................. 324/658; 324/71.5
(58) Field of Classification Search ............ 324/658, 324/649, 600, 348, 410, 71.5, 72, 425, 435, 324/464, 465; 204/400–435
See application file for complete search history.

(56) References Cited

U.S. PATENT DOCUMENTS 3,787,755 A * 1/1974 Goldner ...................... 363/127
4,171,246 A * 10/1979 Hamblen et al. ........ 205/778.5

(Continued)

FOREIGN PATENT DOCUMENTS

DE        100 01 124 C1      6/2001

(Continued)

OTHER PUBLICATIONS

Baumann W H et al: "Microelectronic sensor system for microphysiological application on living cells"; Sensors and Actuators B, Elsevier Sequoia S.A., Lausanne, CH, vol. 55, No. 1, Apr. 25, 1999, pp. 77–89.

(Continued)

*Primary Examiner*—Anjan Deb
*Assistant Examiner*—Hoai-An D. Nguyen
(74) *Attorney, Agent, or Firm*—Dickstein, Shapiro, Morin & Oshinsky, LLP

(57) ABSTRACT

A measuring cell for recording an electrical potential of an analyte situated on the measuring cell. The measuring cell has a sensor, a layer arranged above the sensor and electrically insulating the analyte from the sensor, and an amplifier circuit connected to the sensor on a substrate and having an input stage containing a field-effect transistor or a bipolar transistor, the sensor being at least indirectly connected to a control terminal of the field-effect transistor or of the bipolar transistor. An operating point of the amplifier circuit is set by means of a voltage or a current applied at the control terminal of the field-effect transistor or of the bipolar transistor of the input stage of the amplifier circuit.

50 Claims, 13 Drawing Sheets

U.S. PATENT DOCUMENTS

| | | | |
|---|---|---|---|
| 4,344,150 A * | 8/1982 | McLaughlin | 708/310 |
| 4,963,815 A * | 10/1990 | Hafeman | 205/777.5 |
| 5,309,085 A | 5/1994 | Sohn | |
| 5,336,388 A * | 8/1994 | Leader et al. | 204/403.06 |
| 5,413,690 A * | 5/1995 | Kost et al. | 205/777.5 |
| 5,484,958 A * | 1/1996 | Ogawa | 84/731 |
| 5,846,708 A * | 12/1998 | Hollis et al. | 435/6 |
| 5,965,452 A | 10/1999 | Kovacs | |
| 6,083,710 A * | 7/2000 | Heller et al. | 600/347 |
| 2001/0051109 A1 * | 12/2001 | Anderson et al. | 422/82.01 |

FOREIGN PATENT DOCUMENTS

EP      0 942 259 A1    9/1999

OTHER PUBLICATIONS

Smith R et al: "Electrostatically protected ion sensitive field effect transistors"; Sensors and Actuators, Feb. 1984, Switzerland, vol. 5, No. 2, pp. 127-136.

Keiji Tsukada et al: "ISFET Incorporated in a Differential Amplifier"; Electronics & Communications in Japan, Part II—Electronics, Scripta Technica, New York, NY, USA, vol. 71, No. 3, Mar. 1, 1988, pp. 82-87.

Takahashi K et al: "Bi-MOSFET Amplifier for Integration with Multimicroelectrode Array for Extracellular Neuronal Recording"; IEICE Transactions of Fundamentals of Electronics, Communications and Computer Sciences, Institute of Electronics Information and Comm. Eng. Tokyo, JP, vol. E77-A, No. 2, Feb. 1, 1994, pp. 388-393.

Stett A et al.: "Two-way silicon-neuron interface by electrical induction"; Physical Review E. Statistical Physics, Plasmas, Fluids, and Related Interdisciplinary Topics, American Institute of Physics, New York, NY, USA, vol. 55, No. 2, Feb. 1997, pp. 1779-1782.

Fromherz P: "Interfacing Neurons and Silicon by Electrical Induction"; Ber. Bunsenges. Phys. Chem. 100, No. 7, 1996, pp. 1093-1102.

Vassanelli S et al: "Transistor records of excitable neurons from rat brain"; Applied Physics A 66, 1998, pp. 459-463.

Parak W et al: "The field-effect-addressable potentiometric sensor/stimulator (FAPS)-a new concept for a surface potential sensor and stimulator with spatial resolution"; Sensors and Actuators B-58, 1999, pp. 497-504.

Yeow W.J. et al: "Design of a Single Cell of an ISFET Array Chip", Microelectronics: Technology Today for the Future NA (NA), 1995, pp. 62-67.

Yeow T.C.W. et al: "A very large integrated pH-ISFET sensor array chip compatible with standard CMOS processes"; Sensors and Actuators B 44, 1997, pp. 434-440.

Yeow T.C.W. et al: "Thick-Film Thermistor Array Using a Novel Threshold Conversion Concept"; Sensors and Materials, vol. 10, No. 2, 1998, pp. 77-91.

Vavelidis K. et al: "Design Considerations for a Highly Linear Electronically Tunable Resistor"; IEEE International Symposium on Circuits and Systems, New York, 0-7803-1254-Jun. 1993, 1993, pp. 1180-1183.

* cited by examiner

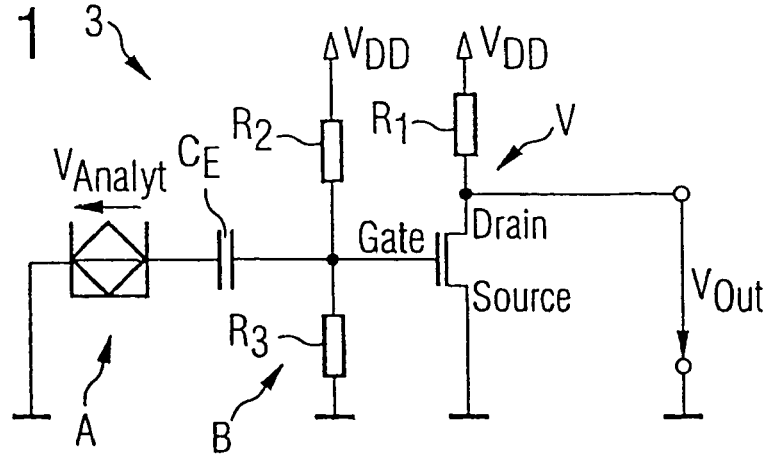
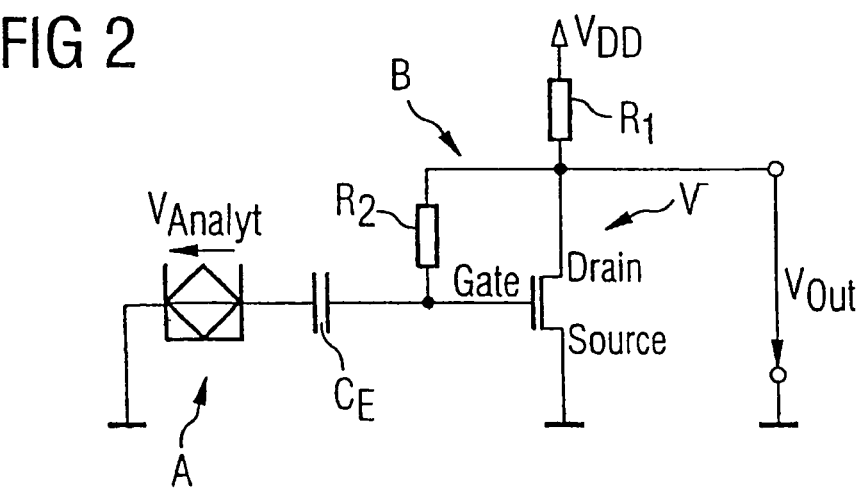
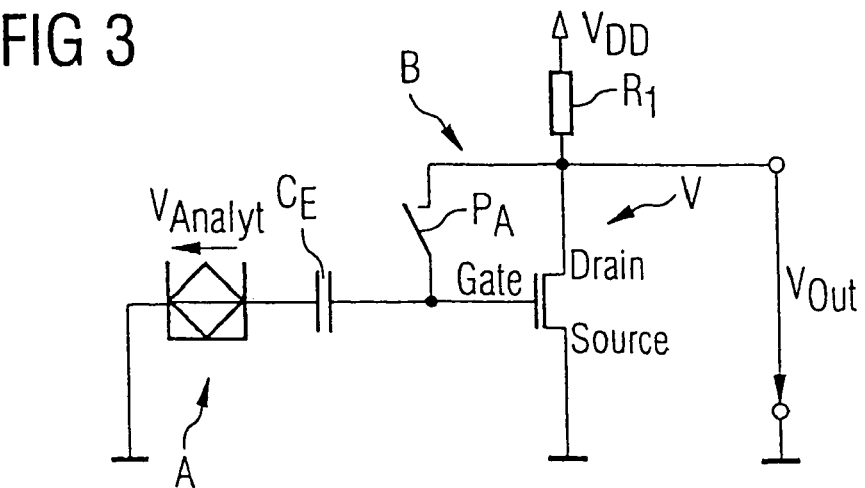

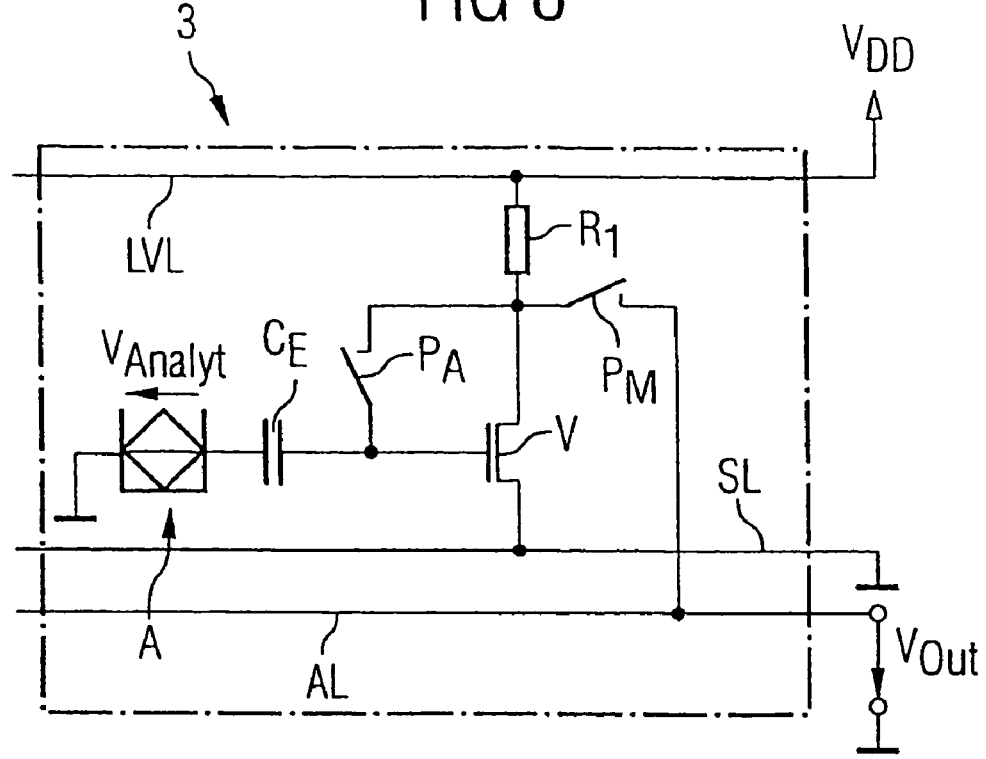
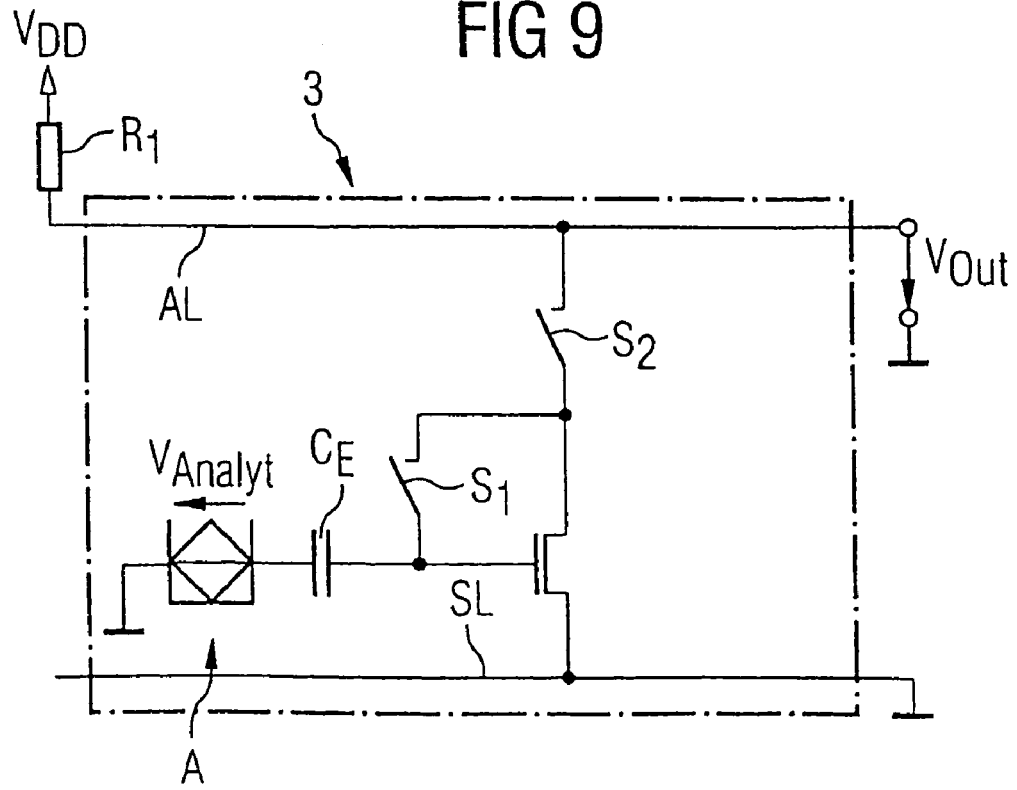

FIG 18
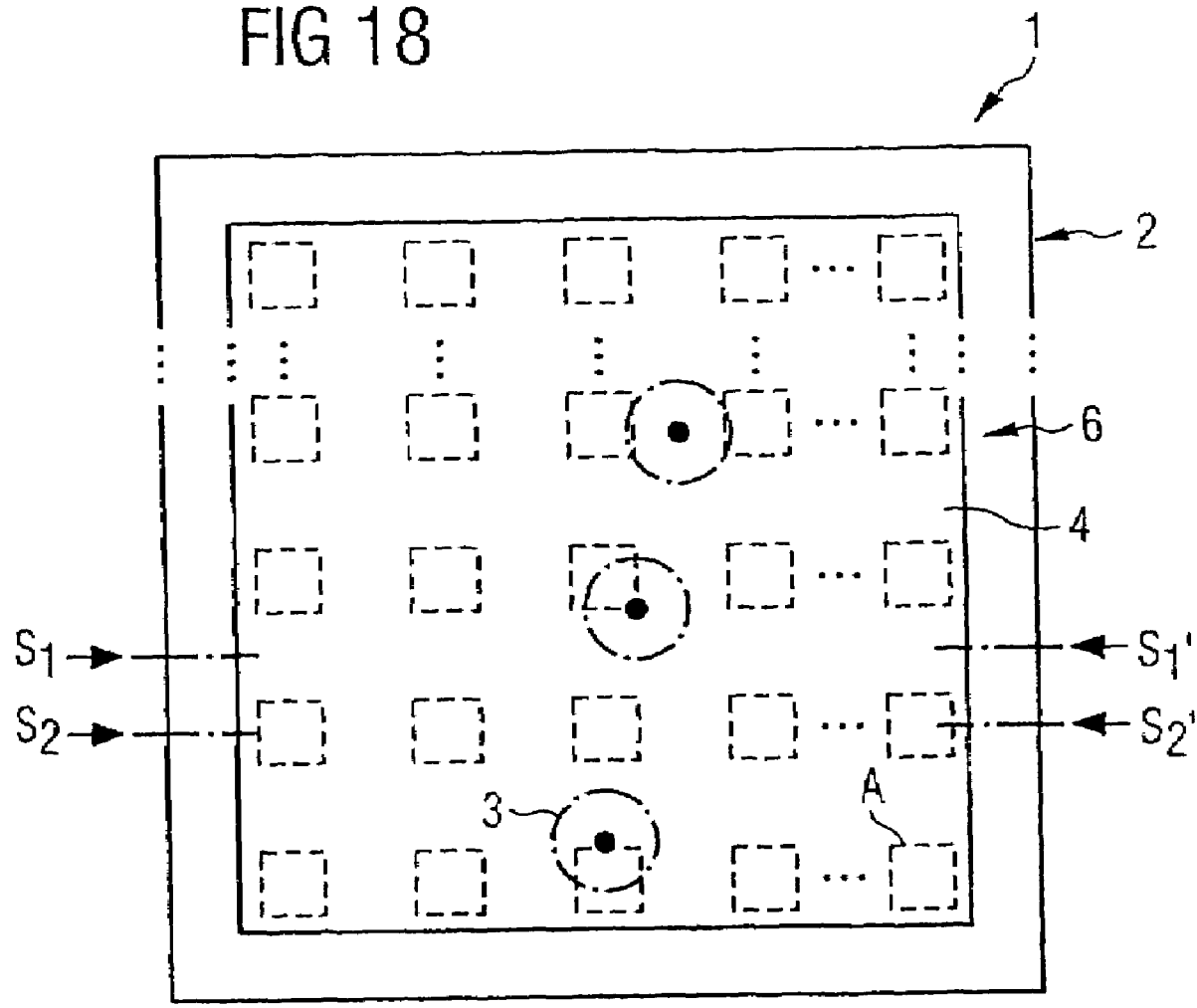
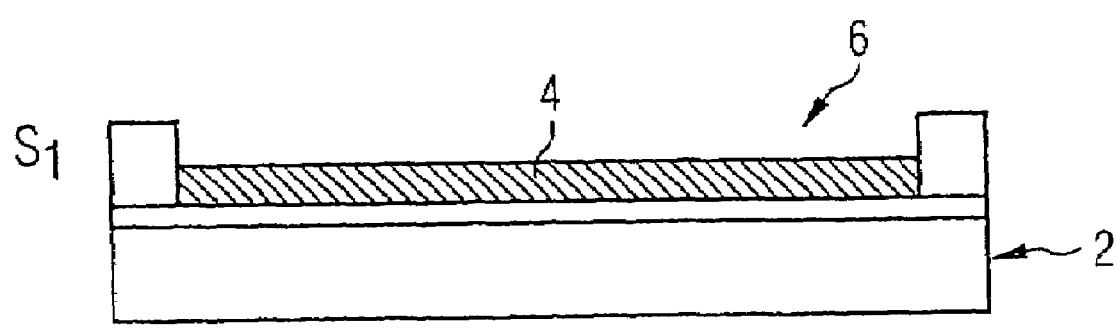
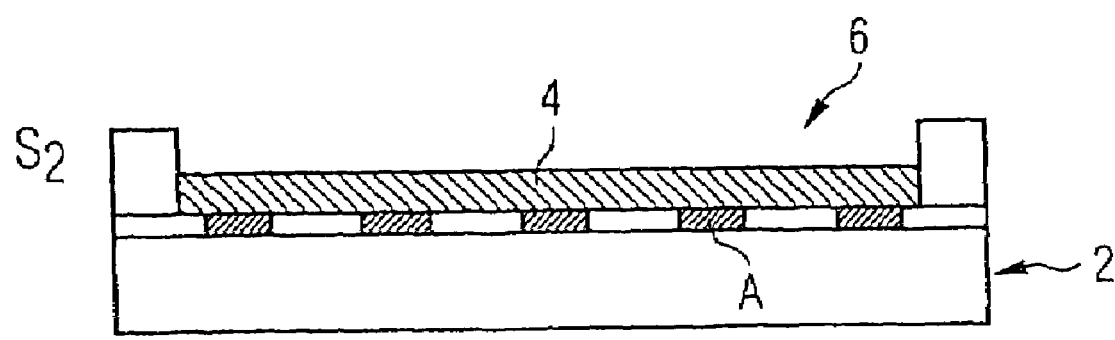

FIG 19
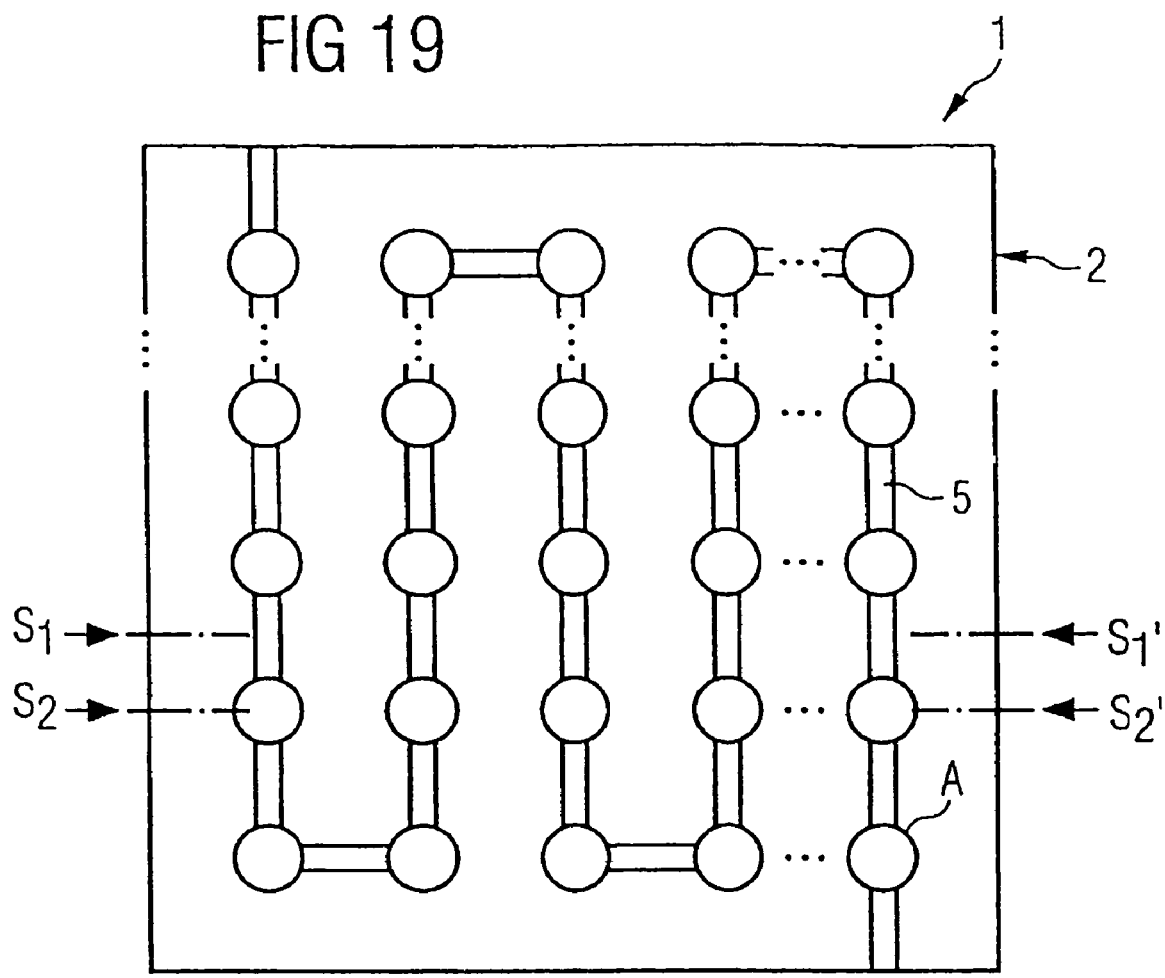
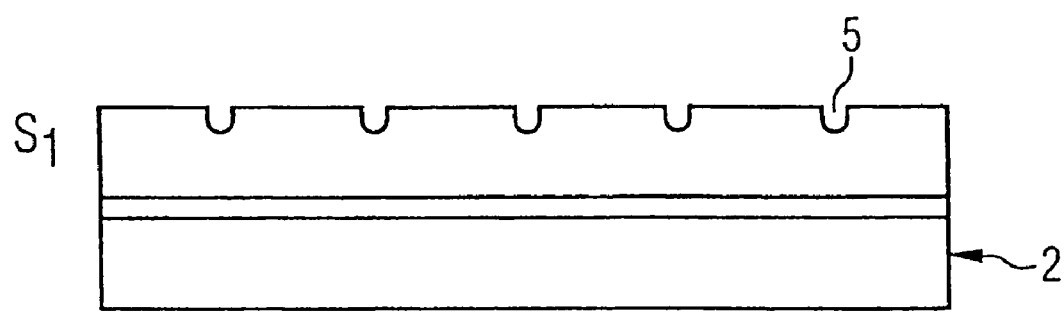
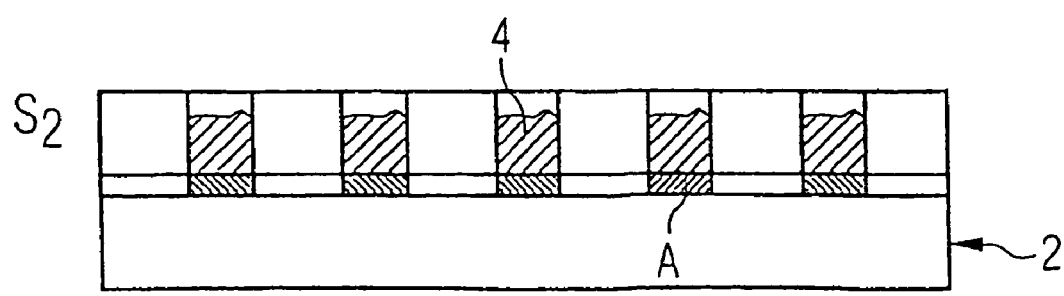

MEASURING CELL AND MEASURING FIELD COMPRISING MEASURING CELLS OF THIS TYPE, USE OF A MEASURING AND USE OF A MEASURING FIELD

CROSS-REFERENCE TO RELATED APPLICATION

This application is a continuation of International Patent Application Ser. No. PCT/DE02/02526, filed Jul. 10, 2002, which published in German on Jan. 23, 2003 as WO 03/006981 A2.

FIELD OF THE INVENTION

The present invention relates to a measuring cell, and more particularly, to a measuring cell for recording an electrical potential of an analyte situated on the measuring cell.

BACKGROUND OF THE INVENTION

In analysis technology or sensor technology, potentiometric measurements are performed, i.e., electrical potentials are measured without impressing a current into the measurement object. Said electrical potentials represent the property of the analyte to be characterized or are generated from the property of an analyte to be characterized by means of a so-called transducer. A sensor for this converts said electrical potentials into electrical signals, for example voltage signals, which are subsequently evaluated. By way of example, in pure medical research, electrodes are used during the potentiometric measurement of extracellular neural signals.

In accordance with K. Takahashi, S. Takeuchi, Bi-MOSFET Amplifier for Integration with Multimicroelectrode Array for Extracellular Neuronal Recording, IEICE TRANS. FUNDAMENTALS, Vol. E77-A, No. 2, 388–393, February 1994, an electrode module is provided for measuring electrical potentials of neurons. The electrode module produced from semiconductor material contains a tapering pointed microelectrode and, at its wide end, a rectangular substrate with an amplifier thereon.

One problem with the electrode module according to K. Takahashi et al. is that it is not possible to simultaneously measure neuron assemblages in a spatially resolved manner, since the tapering pointed microelectrode can only perform point measurements. On account of this, in the case of the present electrode module, the dimensioning of the amplifier is also of secondary importance since no structural space constraints whatsoever result.

P. Fromherz, Interfacing Neurons and Silicon by Electrical Induction, Ber. Bunsenges, Phys. Chem. 100, No. 7, 1093–1102, 1996, discloses a field-effect transistor used as a sensor and serving for electronically reading out neural signals of living cells. In this case, a living nerve cell bears on the insulated, open gate of the field-effect transistor. This sensor can record neural signals of the cell, which are manifested in the form of changes in potential at the cell wall, since these changes in potential control or modulate the channel current of the transistor or the density of the charge carriers present in the channel region between drain and source.

The arrangement disclosed in P. Fromherz was extended in A. Stett et al., Two-way silicon-neuron interface by electrical induction, Physical Review E, Volume 55, Number 2, 1779–1782, February 1997, to the effect that, by means of bidirectional connection, the potential of a nerve cell can be altered by the application of an electrical signal to the arrangement. For this purpose, a control electrode is arranged beside the FET structure in a manner insulated from the latter, which control electrode, by the application of a corresponding electrical signal, causes the nerve cell to change its electrical potential.

S. Vassanelli, P. Fromherz, Transistor records of excitable neurons from rat brain, Appl. Phys. A66 459–463, 1998, shows the previously described arrangements in the application when determining potentials of nerve cells of a rat.

In the case of an external signal gain connected to the above-described sensor, on account of the small signal amplitudes, a poor signal transfer, a poor signal-to-noise ratio, and also a higher sensitivity toward disturbing influences (e.g., leakage fields) and parasitic effects are disadvantageous.

W. J. Parak et al., The field-effect-addressable potentiometric sensor/stimulator (FAPS)— a new concept for a surface potential sensor and stimulator with spatial resolution, Sensors and Actuators, B-58, 497–504, 1999, discloses an array of ion-sensitive field-effect transistors which are constructed on a GaAs substrate and are arranged in rows and columns. In order that the individual transistors can be arranged as closely adjacent as possible, the gates of a FETs arranged in a common column were connected to one another to form a back gate, as were the channels of FETs located in a row. By sequentially tapping columns and rows, it is possible to determine the location of a change in potential within the measuring array.

What is disadvantageous about the arrangement according to W. J. Parak et al. is that the current path has to flow via a series circuit of sensors. As a result, it is not possible to realize large arrays since the series resistance with regard to the selected sensor leads to an attenuation of the signal in accordance with a voltage divider.

Furthermore, a very complicated production process is necessary in order to realize a back gate. Furthermore, a special GaAs technology is used, the material arsenic which is used being highly toxic and the sensor thus only being suitable for a small proportion of possible applications.

T. C. W. Yeow et al., Design of a Single Cell of an ISFET Array Chip, Microelectronics: Technology today for the future, NA (NA) 62–67, 1995, shows an array of ion-sensitive field-effect transistors on a common substrate. In this case, the array does not serve to enable individual transistors to detect local impedances in their surroundings which differ from the impedance acting on the adjacent transistor. Thus, a highest possible resolution of the array is not desired at all. Instead, precisely the measurement sample is to have constant properties across the array, because the array serves as an analog-to-digital sensor: in this case, a threshold value is assigned to each sensor cell designed as a field-effect transistor. The threshold values differ from sensor cell to sensor cell. A comparison circuit checks whether the measurement quantity exceeds the respective threshold value. Thus, an array of binary values which reproduces a specific measured value is produced with regard to a sample covering the array. Read-out circuits are integrated on the substrate.

T. C. W. Yeow et al., A very large integrated pH-ISFET sensor array chip compatible with standard CMOS process, Sensors and Actuators B 44, 434–440, 1997, shows an arrangement according to T. C. W. Yeow et al. developed further. In this case, each sensor row is assigned only one comparator, the threshold values of which can be altered, so that the individual sensors are read sequentially.

T. C. W. Yeow et al., Thick-Film Thermistor Array Using a Novel Threshold Conversion Concept, Sensors and Materials, Vol. 10, No. 2, 77–91, 1998, shows further mechanisms for threshold value evaluation in this regard.

In the case of the arrangements described last, the output values obtained in this way in the individual sensors are summed and averaged. This average value then depends linearly on the measurement quantity.

However, this only enables relatively slow measurements without spatial resolution, since, on the one hand, the entire array has to be covered by the sample in order that all the sensors can record the same quantity and compare it with the assigned threshold values. On the other hand, the read-out mechanisms are complicated and slow, so that the arrangement is only suitable for static measurements.

By contrast, a very high packing density of sensors is necessary for the spatially resolved measurement of, for instance, very small extracellular signals of individual neurons within an assemblage of neurons.

In order to be able to measure the signals of individual neurons, the output signals of the sensors of the array must be able to be read out individually. The distance between adjacent measuring cells—also called pixels hereinafter—which in each case contain the sensor circuits must be smaller than the neurons themselves. However, on the one hand, minimum feature sizes dictated by the production process represent a boundary condition for the production of sensors. On the other hand, statistical fluctuations in the parameters and the noise proportions of the sensor signals increase greatly as the area of the components decreases.

Therefore, in many applications, the components of the sensor circuits have to be given larger than minimum dimensioning in order to guarantee an acceptable signal-to-noise ratio. Thus, pixel circuits have to be realized with a smallest possible number of components in order to achieve a small pitch and good signal-to-noise ratios. Furthermore, it is also necessary to ensure stability, high sensitivity and robustness of the arrangement.

Furthermore, EP 0 942 259 A1 describes a capacitive distance sensor for acquiring a fingerprint image. The sensor has a capacitive element with a first and a second capacitor plate, which are arranged next to one another and whose distance with respect to one another is measured. The sensor furthermore has an inverting operational amplifier, in whose feedback path the capacitive elements are connected.

U.S. Pat. No. 5,309,085 describes a measuring circuit with a biosensor, in which ion-sensitive field-effect transistors are used.

U.S. Pat. No. 5,965,452 discloses a multiplexed active biological electrode array.

O. Limann, Elektronik ohne Ballast: Einführung in die Schaltungstechnik der industriellen Elektronik [Electronics with no ballast: Introduction to the circuit technology of industrial electronics], Franzis-Verlag, 7th edition, pp. 35–38, 1987, describes basic circuits with field-effect transistors.

SUMMARY OF THE INVENTION

Consequently, the invention is based on the problem of providing a measuring cell and also a measuring array having measuring cells which satisfy the requirements set and are robust and universally usable.

The problem is solved by means of a measuring cell and a measuring array having the features in accordance with the independent patent claims. Preferred refinements of the invention emerge from the dependent claims.

The measuring cell integrated into a substrate contains a sensor, also called converter element. The converter element converts an arbitrary measurement quantity into an electrical potential. This also includes simply transmitting an electrical potential.

In this case, the converter element may be conceived of as a series circuit of a controlled source and a capacitance. In this case, the converter element may be designed as a customary or pH-sensitive electrode. A pH-sensitive electrode converts the ion concentration in an aqueous solution into a charge quantity or electrical voltage or potential and thus makes it possible to determine an electrical potential in an aqueous environment.

Furthermore, an amplifier circuit connected to the sensor is arranged on the common substrate.

According to the invention, the amplifier stage is arranged in the measuring cell. This ensures a good signal transfer, and also a good signal-to-noise ratio. The sensitivity toward disturbing influences, e.g., leakage fields and parasitic effects, is low.

On the other hand, given suitable dimensioning of the amplifier stage, the measuring cell also has a small areal requirement, so that it is also possible to achieve high packing densities of measuring cells and it is thus possible to record the potentials even of extremely small samples, in particular also in the assemblage in a spatially resolved manner with the aid of a measuring array.

The measuring cell is distinguished by stability, high electrical sensitivity and mechanical robustness.

Preferably, the input stage of the amplifier circuit in this case contains a transistor integrated on the substrate, the sensor or, if appropriate, the sample itself being at least indirectly connected to a control terminal of the transistor.

This ensures that the electrical potential of the sample which is recorded by the sensor and converted into an electrical signal—preferably a current signal or a voltage signal—is conditioned in such a way that it offers a sufficient resolution for the evaluation and is subsequently less sensitive toward disturbing influences.

The amplifier circuit may be set up in single-stage fashion or in multistage fashion.

In a preferred development, the transistor is designed as a field-effect transistor with source, drain and gate, which is operated in a common-source connection.

In an alternative advantageous development of the invention, the transistor is designed as a bipolar transistor with emitter, collector and base, which is operated in a common-emitter connection.

However, the transistor may also be designed as a Darlington circuit comprising a plurality of subtransistors if a particularly high gain factor is intended to be achieved.

The amplifier circuit preferably contains a load element for setting an operating point of the transistor.

In this case, the load element may be designed as a nonreactive, preferably variable, resistor, as a transistor or as a current source.

In many applications, in this case, the load element is arranged as a constituent part of the amplifier circuit on the common substrate.

This reduces the production outlay.

In other advantageous developments, the load element is arranged outside the substrate.

The area required for the measuring cell can thereby be reduced. With this reduction of the number of components, it is furthermore possible to achieve a small pitch and a good signal-to-noise ratio.

Preferably, the load element is arranged between the drain or the collector of the transistor and a first supply potential. In this case, the first supply potential is usually a positive potential, relative to a second supply potential defined afterward, which is usually designed as ground.

A controllable switch is preferably arranged between the control terminal and the drain or the collector of the transistor, which controllable switch is designed, in particular, as a transistor and is arranged as a constituent part of the amplifier circuit on the common substrate.

In accordance with one refinement of the invention, the amplifier circuit has a feedback via which a suitable voltage or a suitable current is impressed at the sensor electrode.

The feedback is preferably set up as a controlled switch, a low-pass filter, or a unit for externally storing an operating voltage.

In this case, provision is made of a measuring operating phase for measuring the potential of the sample, during which the switch is opened, and of a setting operating phase for setting the operating point of the amplifier circuit, during which the switch is closed. The setting operating phase is defined in the pauses of the measuring operating phases.

The operating point of the amplifier circuit can thus be set anew at short time intervals.

As an alternative to the controllable switch presented, it is also possible to arrange a further load element according to one of the abovementioned variants between the control terminal of the transistor and the drain or the collector of the transistor.

As an alternative, a further load element may be arranged between the control terminal of the transistor and the first supply potential, and a third load element may be arranged between the control terminal and a further supply potential.

The further load element and/or the third load element are preferably arranged on the substrate.

The substrate may have terminals for at least the first supply potential, the further supply potential and the amplified electrical signal of the sensor as output signal of the measuring cell.

The following developments of the invention manifest an advantageous effect, in particular, when they are used within a measuring array.

A further controllable switch may be connected to the drain or the collector terminal of the transistor.

In this case, the further switch may at the same time be arranged between the drain or the collector terminal of the transistor and the load element.

When switched on, said further switch releases the amplified electrical signal for a tapping, thus e.g., to a terminal of the substrate.

Preferably, the further controllable switch is arranged as a constituent part of the amplifier circuit on the substrate.

In an advantageous development of the invention, the sensor of the measuring cell contains a pH-sensitive layer.

Preferably, the measuring cell, for converting an electrical potential of a sample into an electrical signal, contains a field-effect transistor on the substrate as a sensor with gate, source and drain, which is designed in such a way that the sample is arranged above the gate layer during sensor operation and its electrical potential is coupled to a channel current of the field-effect transistor between source and drain.

It is thus possible to record the pH concentration as a parameter of a sample. For its part, the pH concentration supplies an electrical potential which is recorded by the field-effect transistor. By determining the pH concentration, it is also possible to deduce the substance constitution of the sample.

The pH-sensitive layer may be preceded by a substance-selective membrane which only permits specific substances to be measured.

A measuring array contains a multiplicity of the above-described measuring cells on a common substrate. In this case, each measuring cell of a measuring array contains its own amplifier circuit.

With the measuring array, it is also possible to record potentials of extremely small structures such as extracorporeal neurons within a neuron assemblage in a spatially resolved manner.

The measuring array can be fabricated in a cost-effective manner in standard CMOS processes, and enables a good signal-to-noise ratio in conjunction with high spatial resolution and a high packing density. The sensor signals can be measured without the individual sensors mutually influencing one another. A high temporal resolution is also possible.

With regard to the further advantages, reference is made to the explanations concerning the measuring cell.

Preferably, the measuring cells are arranged in rows and columns on the substrate.

This achieves good area utilization and location determination with regard to the measurement object.

On the substrate, it is possible to provide a common source-side connecting line for connecting all the source or emitter terminals either of a cell row or of a cell column.

This means that it is not necessary for each source terminal of a measuring cell to be individually routed toward the outside on the substrate.

Such a common source-side connecting line may be provided for each cell row or cell column, so that the failure protection in the event of one of the lines being interrupted is also optimized in this regard.

Preferably, the substrate has a terminal for each source connecting line, for the connection of each source connecting line to ground potential.

On the substrate, it is possible to arrange a common control line for controlling all the controllable switches either of a cell column or of a cell row.

This means that it is not necessary for each control terminal of a measuring cell to be individually routed toward the outside on the substrate.

Such a common control line may be provided for each cell column or cell row, so that the failure protection in the event of one of the lines being interrupted is also optimized in this regard.

Preferably, the substrate has a terminal for each control line for the connection of a control unit.

Preferably, the substrate has a common further control line for controlling all further controllable switches either of a cell row or of a cell column.

This means that it is not necessary for each control terminal of a measuring cell to be individually routed toward the outside on the substrate.

Such a common further control line may be provided for each cell row or cell column, so that the failure protection in the event of one of the lines being interrupted is also optimized in this regard.

Preferably, the substrate has a terminal for each further control line, for the connection of a control unit. This arrangement enables output signal values to be read out column by column or row by row.

The substrate may have a common output line for connecting all further controllable switches either of a cell column or of a cell row.

This means that it is not necessary for each output of a measuring cell to be individually routed toward the outside on the substrate.

Such a common output line may be provided for each cell column or cell row, so that the failure protection in the event of one of the lines being interrupted is also optimized in this regard.

Preferably, the substrate has a terminal for each output line, for example for the connection of an evaluator.

The substrate may contain a common load-side supply line for connecting all the load elements either of a cell column or of a cell row.

This means that it is not necessary for each terminal of a load element of a measuring cell to be individually routed toward the outside on the substrate.

Such a common load-side line may be provided for each cell column or cell row, so that the failure protection in the event of one of the lines being interrupted is also optimized in this regard.

The substrate preferably contains a terminal for each load-side line, for connection to the positive supply potential.

In an advantageous development, the substrate contains a common connecting line for connecting all further controllable switches either of a cell column or of a cell row.

In this case, such a common connecting line is provided for each cell column or cell row, said connecting line in each case having a terminal on the substrate. A load element is arranged outside the substrate for each cell column or for each cell row. A respective load element is connected to a terminal for a respective connecting line. The substrate has a further terminal for each connecting line, so that an electrical output signal can be tapped off at each further terminal.

In the previous development, a diode may be provided as an alternative to each further controllable switch.

Preferably, the measuring array contains measuring cells having differently prepared sensors. In this case, the sensors of at least two different measuring cells are designed for detecting different parameters or substances of the sample.

With this measuring array, it is possible to simultaneously detect different substances of the sample, in particular on the basis of the pH value thereof. For this purpose, individual sensors may have a pH-sensitive layer. A membrane designed in a manner dependent on the substance to be determined may then be applied to said pH-sensitive layer and converts the substance to be determined into a change in the pH value. The membrane or the transducer may in this case be an enzyme or else be constructed with activatable ion pumps or with even more complex mechanisms. The electrical potential corresponding to the pH concentration is then measured by the sensor configured in this way.

As a result, the simultaneous detection of a multiplicity of different compounds is made possible by means of one measuring array.

In the case of a small number of different sensors for detecting different parameters or substances, the different sensors may also be arranged in a periodic order in the measuring array.

In one advantageous development, the measuring cells form the bottom of a well which receives the sample during measuring operation.

In a further advantageous development, a channel is provided above the measuring cells for receiving the sample during measuring operation.

According to the invention, a proposed measuring cell may also be used to apply an electrical potential to a sample by the application of an electrical signal to the amplifier circuit.

According to the invention, a proposed measuring array may also be used to apply electrical potentials to a sample in a spatially resolved manner by the application of electrical signals to the amplifier circuits of the individual measuring cells.

The invention thus enables a so-called bidirectional communication with regard to a measuring cell. In this case, a voltage or a voltage pulse is applied to the output terminal of the amplifier circuit of the measuring cell in order thus, in the sample, e.g., in a neurochip, to excite neurons or to initiate specific chemical reactions.

A preferred field of application of the invention is pure medical research and pure pharmaceutical research. In these disciplines, there is great interest in measuring signals of a plurality of neurons extracellularly (nondestructively) using an array of sensors.

In pure research, this will enable information about the function of biological neural networks and, in the long term, will enable the development of neuro-prostheses.

In pharmaceutics, there is the possibility of investigating neurotoxicity and exhibitory and inhibitory effects of medicaments. In this case, the invention enables, in particular, investigations of the behavior of cells and cell assemblages, e.g., with regard to intercellular communication or reaction to specific stimuli, such as the influence of medicaments and substances, directly at the cells. In this case, the measuring result is present in a short measuring time, with high reliability and correlation between stimulation and measuring result.

A further application of the invention may be effected in environmental technology, where sensors are developed with cells as transducers for summation factors, such as, for example, for water quality.

Furthermore, the development of special cells which react specifically to specific substances is also conceivable. In this case, analysis technology in its entirety is opened up as a field of application.

Clearly, the invention can be seen in the fact that a single-stage or multistage amplifier circuit is provided in a respective measuring cell, the operating point of which amplifier circuit can be set by means of a load element as feedback element. This makes it possible to compensate for the parameter fluctuations of the amplifier circuit by means of the load element as feedback element.

BRIEF DESCRIPTION OF THE DRAWINGS

Exemplary embodiments of the invention are illustrated in the figures and are explained in more detail below.

FIG. 1 shows a first electrical circuit diagram of a measuring cell according to the invention;

FIG. 2 shows a second electrical circuit diagram of a measuring cell according to the invention;

FIG. 3 shows a third electrical circuit diagram of a measuring cell according to the invention;

FIG. 8 shows an eighth electrical circuit diagram of a measuring cell according to the invention, provided for arrangement in a measuring array;

FIG. 9 shows a ninth electrical circuit diagram of a measuring cell according to the invention, provided for arrangement in a measuring array;

FIG. 18 shows a first measuring array according to the invention in plan view and in two sectional views;

FIG. 19 shows a second measuring array according to the invention in plan view and in two sectional views.

DETAILED DESCRIPTION OF THE PREFERRED MODE OF THE INVENTION

Figure 4:
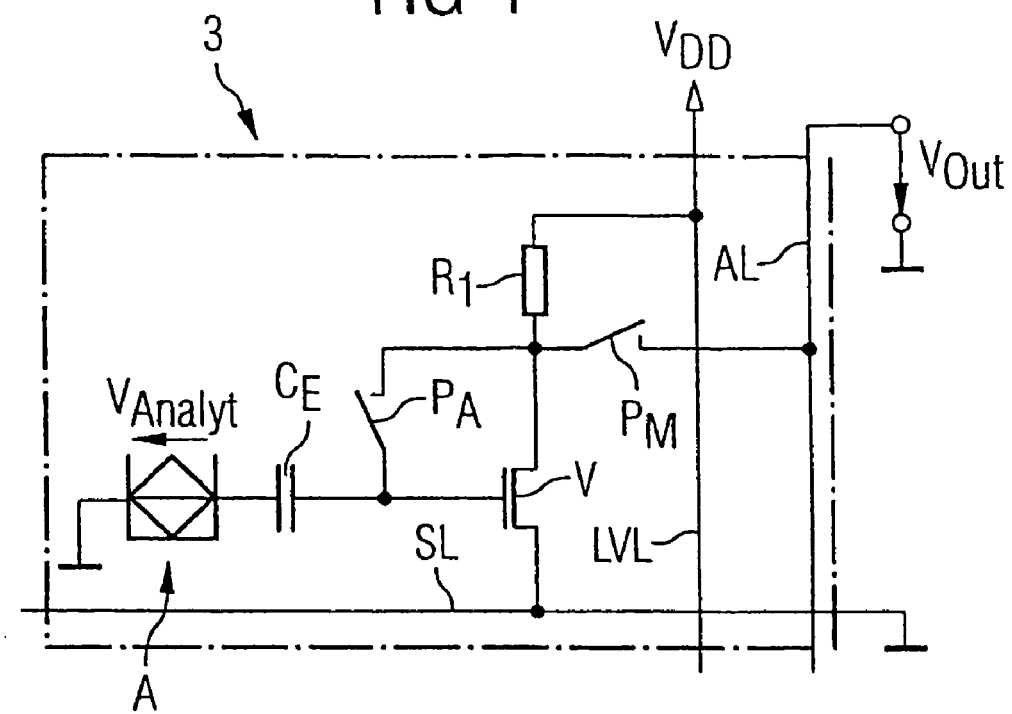
FIG. 4 shows a fourth electrical circuit diagram of a measuring cell according to the invention, provided for arrangement in a measuring array.
Figure 5:
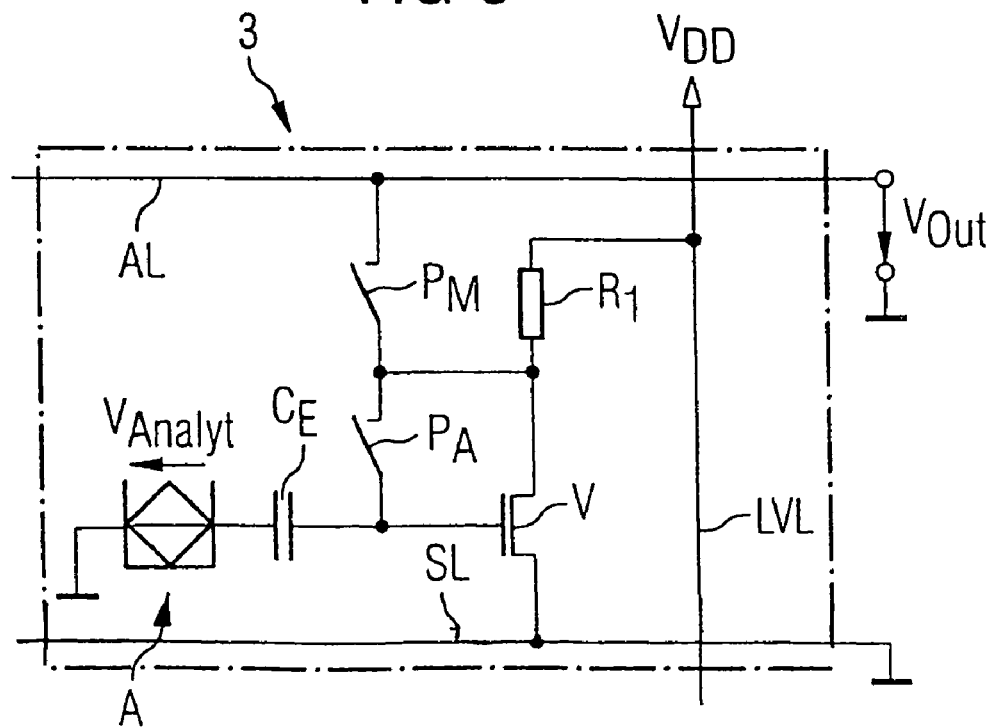
FIG. 5 shows a fifth electrical circuit diagram of a measuring cell according to the invention, provided for arrangement in a measuring array.

Identical elements and quantities in the figures are provided with the same reference symbols.

FIG. 1 shows an electrical circuit diagram of a measuring cell 3 according to the invention with an equivalent circuit diagram of a sensor A for converting a potential, preferably the potential of a neuron, into an electrical sensor signal $V_{analyte}$, that is to say preferably a voltage signal. In this case, the sensor A is designed as a field-effect transistor having gate, source and drain. The sample is arranged above the gate layer during sensor operation, preferably bears on an insulator layer constructed on the gate layer and with its electrical potential controls a channel current of the field-effect transistor between source and drain. The change in the potential or the property of a sample/analyte which is to be detected is thus modeled via a change in the voltage $V_{analyte}$ at the sensor A.

The sensor A is connected to ground on one side and, on the other side, via a DC-voltage-decoupling capacitance $C_E$, the capacitance of the electrode, to an amplifier circuit B with a single-stage amplifier. CMOS technology is used.

Sensor A and amplifier circuit B are arranged in integrated fashion on a common substrate.

The amplifier circuit, operated as a preamplifier, contains an n-type MOS field-effect transistor V having gate, source and drain, which is operated in a common-source connection. The operating point of the transistor V is set via the load elements R1 to R3 designed as resistors. The resistor $R_1$ connects the drain to a first supply potential $V_{DD}$. The operating point of the gate voltage of the transistor V is set via the voltage divider formed by R2 and R3, in the case of which the resistor $R_2$ connects the gate to the supply potential $V_{DD}$ and the resistor $R_3$ connects the gate to a further supply potential, here to the ground potential.

The low-frequency small-signal gain of the transistor V results to an approximation from the product of the transconductance of the transistor $g_m$ and the resistance $R_1$. The voltage component amplified by the transistor V is the product of the voltage of the signal source $V_{analyte}$ with the quotient of the gate capacitance $C_G$ and the complex sum of the capacitance of the electrode $C_E$, the gate capacitance $C_G$ and the resistances $R_2$ and $R_3$. For frequencies which are not very low, this value approximates to the quotient of $C_E$ and the sum of gate capacitance $C_G$ and $C_E$. The total low-frequency transfer function $H_0$ then results as:

$$H_0 = \left(\frac{V_{Out}}{V_{analyte}}\right) \equiv \left(\frac{C_G}{(C_E + C_G)}\right) \cdot g_m \cdot R_1. \quad (1)$$

FIG. 2 shows a second electrical circuit diagram of a measuring cell according to the invention. In contrast to the circuit diagram according to FIG. 1, the load element $R_2$ designed as a resistor connects the gate and drain of the amplifier V. It serves as a feedback resistor. The load element $R_3$ from the circuit diagram according to FIG. 1 is dispensable.

In the exemplary embodiment in accordance with FIG. 2, operating parameter fluctuations—in particular process-dictated and local stochastic operating parameter fluctuations—of transistor V and load resistor $R_1$ are taken into account and automatically compensated for in the definition of the operating point. Furthermore, the space requirement on the substrate is reduced by virtue of a smaller number of resistors compared with the amplifier circuit B according to FIG. 1.

For the consideration of the operating point that is set, equilibrium conditions are considered, i.e., time-dependent signals are disregarded. The gate voltage thus corresponds to the drain voltage. Disregarding the output conductance, the following constitutive equation holds true for the transistor V:

$$I_{D0} = k \cdot (V_G - V_{Th})^2. \quad (2)$$

From Kirchhoff's voltage law, for the gate voltage it follows that:

$$V_G = V_{DD} - I_{D0} \cdot R_1. \quad (3)$$

Consequently, the gate voltage can be eliminated from the constitutive equation of the transistor and the drain quiescent current of the transistor V can be specified as follows:

$$I_{D0} = \frac{1}{R_1} \cdot \left(V_{DD} - V_{Th} - \frac{1}{R_1 \cdot k} \cdot \left(\sqrt{1 + 2 \cdot R_1 \cdot k \cdot (V_{DD} - V_{Th})} - 1\right)\right). \quad (4)$$

As emerges from equation (4), the quiescent current of the transistor decreases approximately hyperbolically with increasing resistance $R_1$. This approximately hyperbolic decrease in the current given by the quotient of current and voltage at the resistor $R_1$ is primarily based on the increase in the divisor of the quotient with increasing resistance.

However, with increasing resistance, there is also a slight increase in the voltage drop at the resistor and thus the numerator of the quotient, and therefore the deviation from the hyperbolic profile. The quiescent current, which determines the transconductance $g_m$, can thus be set by means of R1.

In concrete terms, a weaker than linear decrease in the transconductance $g_m$, which influences the gain, results with the constitutive equations of the transistor. This is in turn attributable to the decrease in the gate or drain voltage and the resultant decrease in the transconductance of the transistor with increasing resistance $R_1$ (cf. equation (5)):

$$g_m = k \cdot \left( \frac{V_{DD} - V_{Th}}{\sqrt{1 + 2 \cdot R_1 \cdot k \cdot (V_{DD} - V_{Th})} - 1} - \frac{1}{R_1 \cdot k} \right). \quad (5)$$

The effect on which the small-signal gain is based can be explained relatively simply if the feedback via the resistor $R_2$ is initially disregarded, the capacitance of the electrode in the limiting transition is considered to be arbitrarily well conducting and the drain current of the transistor in FIG. 2 is considered to be dependent solely on the gate voltage, that is to say the output conductance is disregarded. The small-signal gain is the quotient of the change in the output voltage with respect to the change in the input voltage, that is to say the quotient of the change in the drain voltage with respect to the change in the gate voltage.

A slight change in the gate voltage $\Delta V_G$ results in a change in the drain current $$\Delta I_D = -g_m \cdot \Delta V_G. \quad (6)$$

This change in current brings about a change in the voltage drop at the resistor or drain terminal of $R_1 \cdot \Delta I_D$.

Thus, to a first approximation, the low-frequency small-signal gain $h_0$ results as:

$$h_0 = \frac{\Delta V_D}{\Delta V_G} = g_m \cdot R_1. \quad (7)$$

If the output conductance of the transistor is taken into account, then the gain of the transistor falls only to an insignificant extent since the output conductance is considerably less than the reciprocal of the resistance $R_1$.

Furthermore, the frequency response of the circuit is also of interest. A minimum requirement of the frequency response is the transmission of the frequency components which lie in the bandwidth to be considered. What is desirable, if appropriate, is the attenuation of the components in those frequency ranges which contain no useful signal, that is to say exclusively impair the signal-to-noise ratio. Upon consideration of the circuit, it becomes clear that the frequency response of the circuit is determined by a plurality of factors. Firstly, the capacitance of the electrode forms a capacitive voltage divider with the other capacitances at the gate node.

On account of the very small signals, said voltage divider must be dimensioned suitably in order to avoid a further attenuation of the signals. For this purpose the capacitance $C_E$, by means of which the sensor A and gate are connected, should have a magnitude at least similar to that of the gate capacitance. The changes in gate voltage are amplified at the drain node and fed back to the gate node again via the RC element comprising R2 and the capacitances at the gate node. Since the circuit constitutes an inverting amplifier, this feedback is a negative feedback. As the negative feedback increases, the gain decreases. In order to avoid this in the passband frequency range, the limiting frequency of said feedback must be significantly less than the lower desired limiting frequency of the amplifier. Furthermore, the frequency response is additionally influenced by the output resistance and the parasitic line capacitance to be driven, which the amplifier must be able to drive.

One essential effect of the feedback is that the operating point of the circuit becomes less sensitive toward process-dictated fluctuations, for example in the resistances defining the operating point, in comparison with the measuring cell according to FIG. 1, since the DC component of the gate voltage of the transistor is defined by means of the DC component of the drain voltage, and the transistor thus always has an operating point in the saturation region.

In the case of the measuring cell according to FIG. 3, in comparison with the measuring cell according to FIG. 2, the further load element $R_2$ is replaced by a controllable switch $P_A$. If the switch $P_A$ is closed, then the capacitances situated at the gate are charged to the voltage at the drain node and an operating point is thus set for the drain voltage. This process takes place in recurring setting phases lying between measuring operating phases.

In the measuring operating phases, the controllable switch $P_a$ is open and thus corresponds to an extremely high feedback resistance. The switch $P_a$ can readily be realized in the form of a transistor. During operation, measuring operating phases and setting phases alternate, i.e., the overall system does not operate completely time-continuously.

As already mentioned, the arrangement of the measuring cells in an array is expedient for specific applications. The array comprises individual measuring cells, also called pixels, which contain the sensor, amplifier, connecting elements and, if appropriate, addressing elements. If a multiplicity of sensors are intended to be realized on an area that is as small as possible on account of necessities that have already been mentioned or on account of economic reasons, then it is neither possible to realize a complete multistage amplifier in each measuring cell, nor is it possible for each preamplifier situated in a measuring cell to be fixedly connected to an amplifier situated outside the array without causing the area requirement to increase greatly and losing spatial resolution in the process.

Various measuring cells for use in a measuring array are proposed with reference to FIGS. 4 to 9. The arrangement of identical measuring cells one beside the other and one below the other results in measuring arrays illustrated in FIGS. 12 to 17.

The measuring cells in FIGS. 4 to 9 are outlined in a dotted manner; likewise outlined in a dotted manner are the individual measuring cells within the measuring arrays. In this case, however, the measuring cells of a measuring array are applied on a common substrate. In this case, the outline of a measuring cell according to one of FIGS. 4 to 9 may also identify the substrate boundaries. However, when measuring cells according to FIGS. 4 to 9 are used in a measuring array, the dotted line usually only identifies the measuring cell but not the substrate boundary.

The measuring cell illustrated in FIG. 4 is geared to a measuring array with measuring cell rows and measuring cell columns, in which the source terminals are connected row by row to the ground potential. A source-side connecting line SL is used for this purpose. The resistors R1 are fixedly connected column by column to the supply potential $V_{DD}$ via a load-side supply line LVL. The orientation of the connecting lines is generally arbitrary for these nodes connected to ground and the supply potential $V_{DD}$. In other words, the source-side connecting line SL may also connect all the cells of a column, and the load-side supply line may also connect all the cells of a row.

With the switch $P_A$ open, the transistor V operates in a common-source connection, that is to say effects an amplification of the AC component of the equivalent source $V_{analyte}$.

Furthermore, a further controllable switch $P_M$ is provided. If the further switch $P_M$ is chosen such that it can be driven row by row, then the output signals $V_{out}$ of individual measuring cells can be read out row by row. For this purpose, the further switch $P_M$ in the relevant measuring cells is closed, the drain terminal of the transistor V is connected to an output line AL that connects the measuring cells column by column, and the output signal $V_{out}$ can then be processed further at the edge of the measuring array.

In the case of the measuring cell according to FIG. 5, provision is once again made of a common source-side connecting line SL for connecting the source terminals of a pixel row to ground. The load-side supply line LVL also corresponds to that from FIG. 4. By contrast, an output line AL is now provided, which connects the further switches $P_M$ of all the cell rows to one another. The measuring cells 3 can thus be read column by column by the driving of the further controllable switches $P_M$ of a column.

Figure 6:
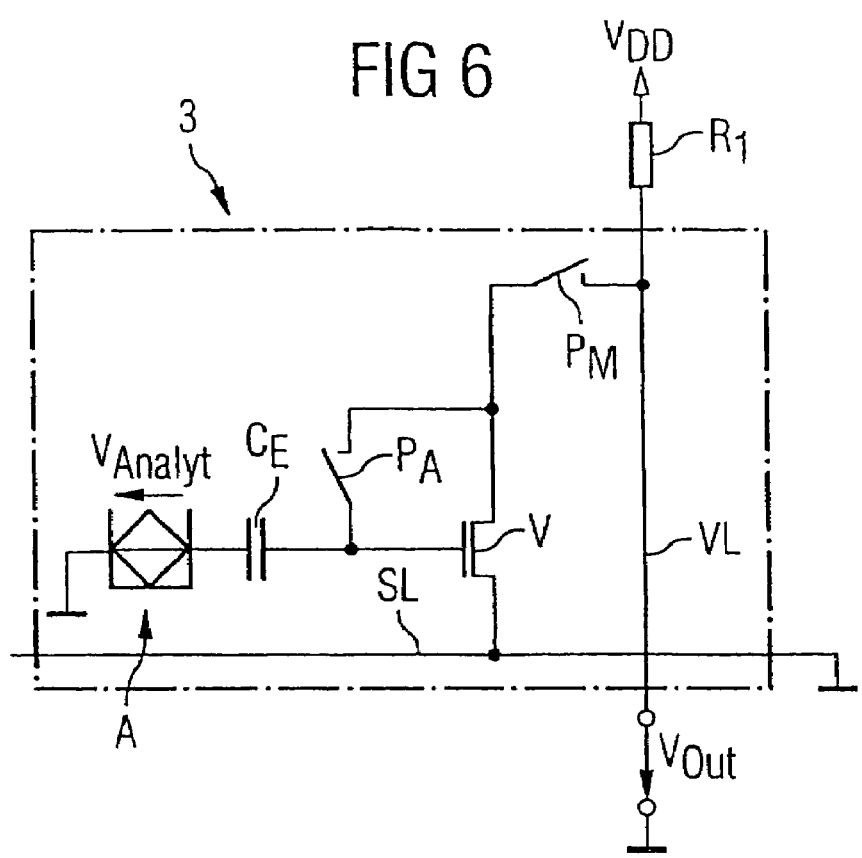
FIG. 6 shows a sixth electrical circuit diagram of a measuring cell according to the invention, provided for arrangement in a measuring array.

In accordance with FIG. 6, the load element $R_1$ may also be arranged outside the measuring cell 3, i.e., here also outside the substrate, if the further switch $P_M$ that can be driven row by row is arranged between load element $R_1$ and transistor V. The area extent of the measuring cell 3 is reduced since the area requirement for a resistor for each measuring cell is obviated. A better spatial resolution is thus achieved with a measuring array having measuring cells according to FIG. 6. Furthermore, a regulation of the resistor with the use of a variable resistor and thus a gain that can be set individually for each measuring cell are then also possible.

In this case, provision is once again made of a common source-side connecting line SL for connecting the source terminals of a pixel row to ground. Furthermore, a connecting line VL is provided between the load element $R_1$ and the output signal tap $V_{out}$. The further controllable switch $P_M$ is connected to said connecting line VL. When further measuring cells of this type according to FIG. 6 are arranged to form a measuring array, all the further controllable switches $P_M$ of a column are connected to the connecting line. The measuring cells can thus be read row by row by the driving of the further controllable switches $P_M$ of a row.

Figure 7:
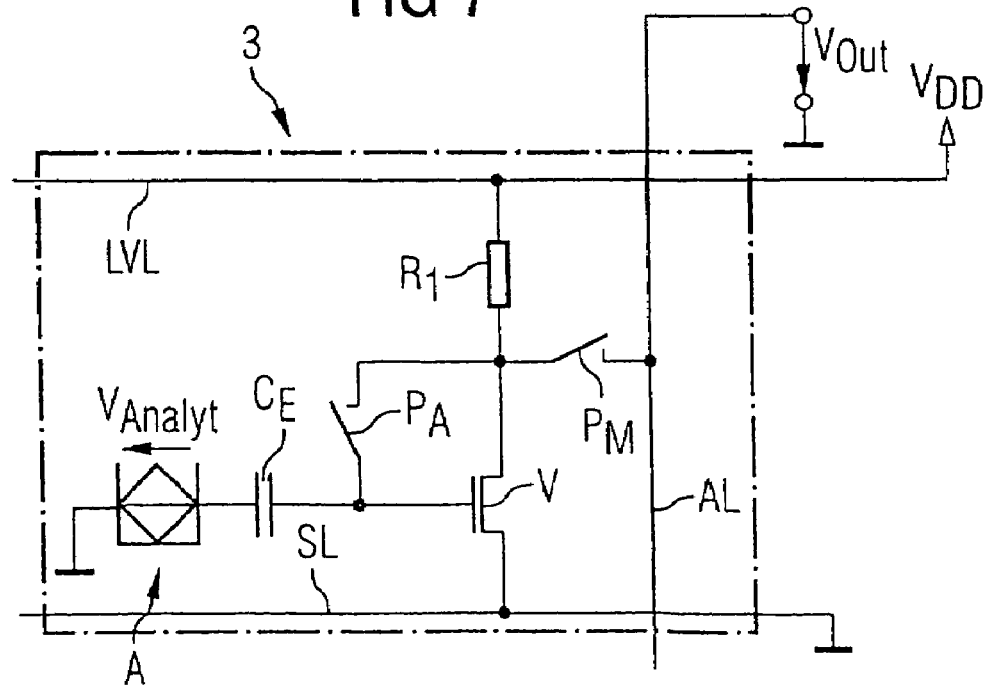
FIG. 7 shows a seventh electrical circuit diagram of a measuring cell according to the invention, provided for arrangement in a measuring array.

The measuring cell according to FIG. 7 essentially corresponds to the measuring cell according to FIG. 4. Provision is once again made of a common source-side connecting line SL for connecting the source terminals of a pixel row to ground. Furthermore, provision is once again made of an output line which connects the further controllable switches $P_M$ of all the cell rows to one another. The measuring cells can thus be read row by row by the driving of the further controllable switches $P_M$ of a row. However, the load-side supply line LVL is now provided for connecting the load elements $R_1$ of a cell row rather than for connecting the load elements $R_1$ of a cell column.

Compared with the measuring cell according to FIG. 7, in the case of the measuring cell according to FIG. 8, the output line AL is now provided for connecting further controllable switches $P_M$ of a cell row, compared with the connection of a cell column according to FIG. 7. The measuring cells can thus be read column by column by the driving of the further controllable switches $P_M$ of a column.

FIG. 9 basically shows a measuring cell according to FIG. 6 with an external load element $R_1$. In this case, however, the connecting line is provided for the connection of all the further controllable switches $P_M$ of a row, not of a column in accordance with FIG. 6. The measuring cells can thus be read row by row by the driving of the further controllable switches $P_M$ of a column. With regard to the advantages of such an arrangement, reference is made to the explanations concerning FIG. 6.

Figure 10:
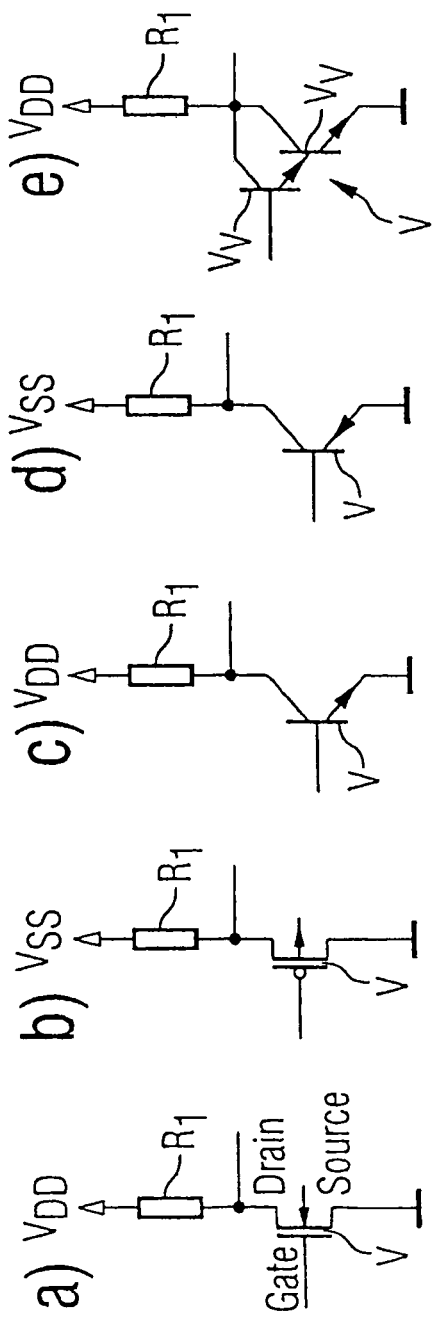
FIG. 10 shows exemplary embodiments of a transistor of the amplifier circuit arranged on the substrate.

FIGS. 10 a) to 10 e) show a detail from the amplifier circuit according to the invention with in each case a load element $R_1$ and a transistor element V between the supply potential $V_{DD}$ and the ground potential. The illustrations serve to demonstrate the alternative use of different transistor elements V as an essential element of the amplifier circuit according to the invention.

In this case, FIG. 10 a) shows the use of an n-type field-effect transistor, FIG. 10 b) shows the use of a p-type field-effect transistor, both in a common-source connection, FIG. 10 c) shows the use of an npn-type bipolar transistor, FIG. 10 d) shows the use of a pnp-type bipolar transistor, both in a common-emitter connection, and FIG. 10 e) shows the use of a Darlington circuit containing two subtransistors VV.

All the circuit variants presented in the remaining figures use n-type MOSFETs, as portrayed in FIG. 10 a).

However, in all the circuit variants, it is possible, both with regard to amplifying transistors and with regard to switching transistors, also to use p-type MOSFETs according to FIG. 10 b), npn-type bipolar transistors according to FIG. 10 c), pnp-type bipolar transistors according to FIG. 10 d) or similar amplifier components.

In principle, a cascading in accordance with the Darlington circuit illustrated in FIG. 10 e) is also conceivable. In all the bipolar variants, a time-discrete negative feedback is not possible. A time-continuous negative feedback with a resistor between collector and base nodes is possible, by contrast, since the base current required for the operation of the circuit is supplied via such a resistor.

Figure 11:
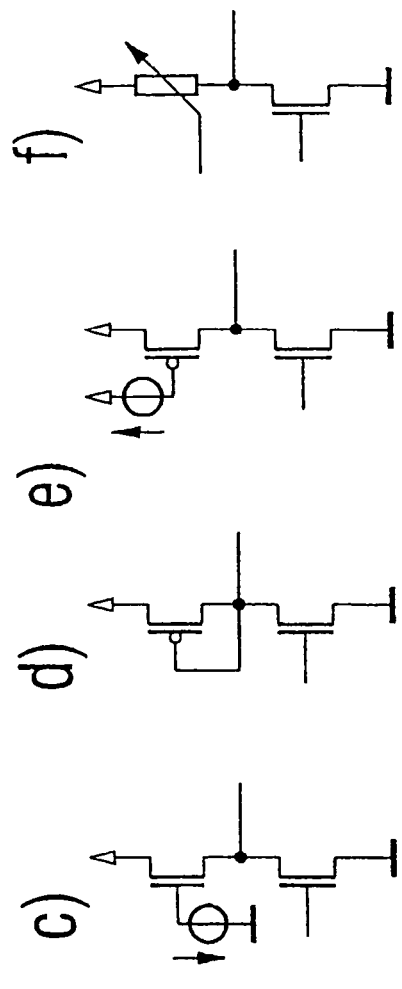
FIG. 11 shows exemplary embodiments of a load element of the amplifier circuit arranged on the substrate.

FIGS. 11 a) to 11 e) show a detail from the amplifier circuit according to the invention with in each case a load element $R_1$ and an n-type field-effect transistor V in a common-source connection between the supply potential $V_{DD}$ and the ground potential.

The illustrations serve to demonstrate the alternative use of different load elements $R_1$. In this case, FIG. 10 a) shows the use of a nonreactive resistor as load element $R_1$, FIG. 11 b) shows the load element $R_1$ in the form of a transistor of the same conductivity type as the amplifier transistor V, the gate voltage of which is identical to the drain voltage, FIG. 11 c) shows the use of a transistor according to FIG. 11 b), the gate voltage of which is defined by a voltage source, FIG. 11 d) shows the use of a transistor of the complementary conductivity type to that of the amplifier transistor V, the gate of which is connected to the drain, FIG. 11 e) shows the use of a transistor according to FIG. 11 d), the gate voltage of which is defined by a voltage source, and FIG. 11 f) shows the use of another realization of a controllable or non-controllable load element.

All the circuit variants presented in the remaining figures use nonreactive resistors as load elements, as depicted in FIG. 10 a). As already discussed, the low-frequency small-signal gain in this case results from the product of the transconductance of the amplifying transistor and the magnitude of the resistor.

However, in all the circuit variants, it is also possible to use a load element in the form of a transistor of the same conductivity type in accordance with FIG. 11 b). Since drain voltage and gate voltage are identical, the result is an operating point in the saturation region or an approximately quadratic relationship between current and voltage which, however, in the operating range, to a first approximation corresponds to the characteristic of a resistor.

Ultimately, the low-frequency small-signal gain results approximately from the quotient of the transconductance of the lower transistor and of the upper transistor. As an alternative to this, it is possible to use a transistor of the complementary conductivity type as in accordance with FIG. 11 d) or for the gate voltage also to be defined by means of a voltage source as illustrated in FIG. 11 c) or 11 e). In principle, any other realization variant of a non-controllable or controllable load element in accordance with FIG. 13 f) is suitable.

As an example of a controllable resistor, reference shall be made here to publication K. Vavelidis, Y. Tsividis, IEEE International Symposium on Circuits and Systems, New York, 0 7803 1254 6/93, 1180–1183, 1993.

The gain of the amplifiers in the individual pixels then also becomes controllable.

It shall once again be expressly mentioned at this point that all the resistor elements described, for example also the voltage divider $R_2/R_3$ from FIG. 1, can be realized with different load elements than nonreactive resistors.

Figure 12:
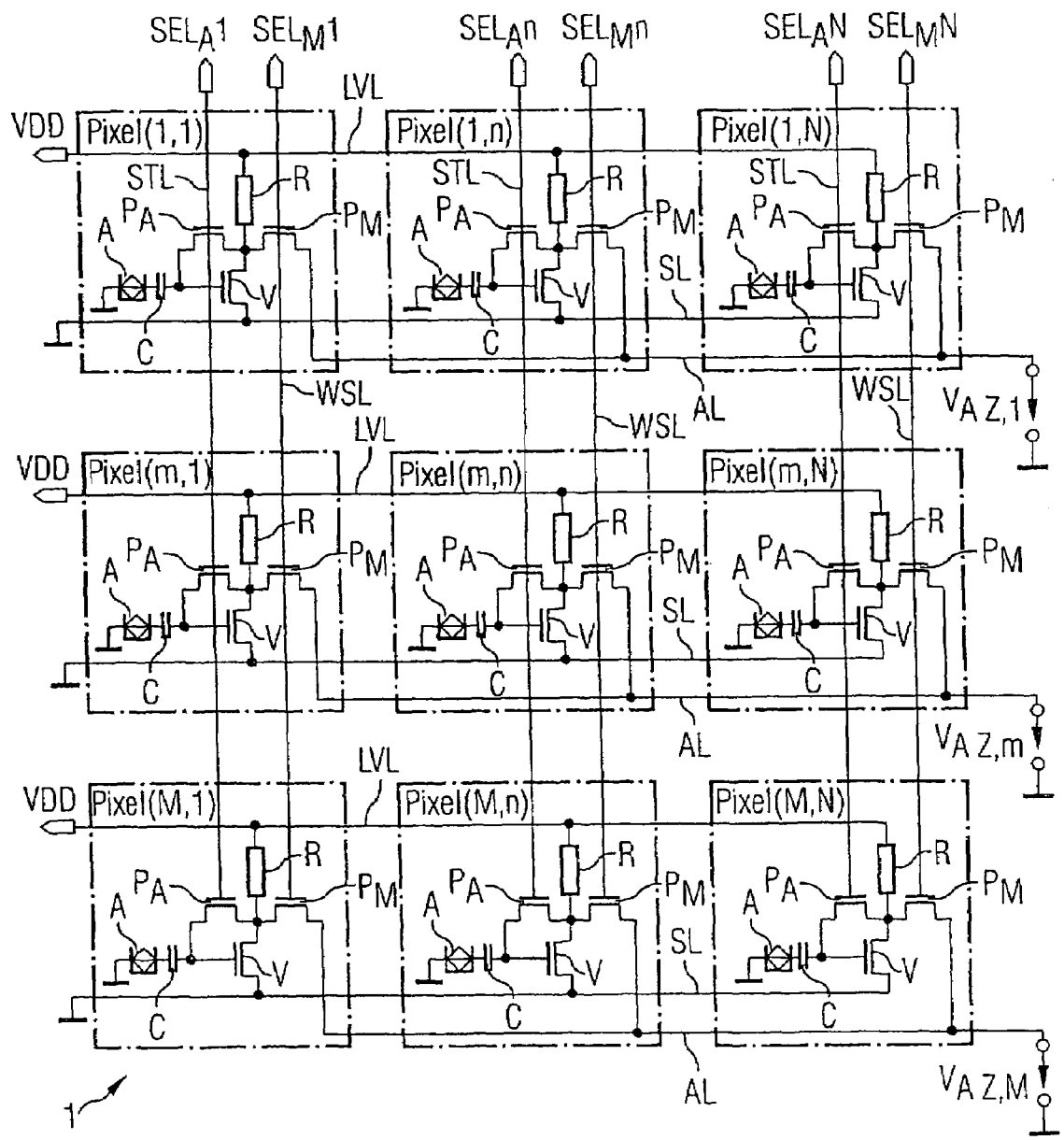
FIG. 12 shows a first electrical circuit diagram of a measuring array according to the invention.

FIG. 12 shows a measuring array having 3×3 measuring cells, also designated by the term "pixel" in the figure. The measuring cells 3 used correspond to the measuring cell construction according to FIG. 8.

The resetting or setting function of the switch $P_A$ is realized by means of the switching or pass transistor, and the further switch $P_M$ for measurement is realized by means of a switching transistor. In principle, these transistors may also be of complementary conductivity type, but the area then becomes significantly larger on account of the required wells.

Ground potential and respectively first supply potential $V_{DD}$ are applied to the load elements R and the source terminals via the horizontal—and thus pixel-row-connecting—source connecting lines SL and load-side connecting lines LVL. The potential difference between these potentials, which may also differ from the operating voltage of the chip, is thus dropped across the series circuit of the resistor R and the transistor V.

The operating point of the amplifiers V in the individual pixels is set during the setting phase which precedes a measuring phase. For this purpose, all the switches $P_A$ are activated by the operating voltage being applied to the terminal $SEL_A$ of the control lines STL for the switches $P_A$. A respective control line S1 connects all the control terminals of the switches $P_A$ of a pixel column. Via the switch $P_A$ gate and drain of the transistor V are thus short-circuited and a stable operating point is set in all the pixels. Said operating point lies in the saturation region since the voltage at the gate-source capacitance is equal to the drain-source voltage. At the end of the setting phase, the transistors $P_A$ are switched to high impedance again. The transistor V then amplifies.

An alteration of the investigated property of the sample leads to a change in voltage at the sensor and thus at the gate capacitance of the transistor V or a change in the gate voltage, which results in a change in the drain voltage amplified approximately by the factor $$-R \cdot g_m \qquad (8)$$

In the configuration illustrated in FIG. 12, this drain voltage can be read out simultaneously or in parallel for a pixel column n. For this purpose, all the switches $P_A$ which are not situated in the n-th column are turned off. For this purpose, the corresponding n-type transistors are controlled with a low level at the terminals $SEL_M$ of the further control lines WSL which connect the further switches $P_M$ of a pixel column. The further switches $P_M$ of the n-th column are activated. As a result, the drain voltages $V_A$ of the transistors V in the n-th column are present on horizontally running output lines AL and can be read out.

The bidirectional signal transfer of a pulse to a sample is possible insofar as it is not only possible for the pixels to be read but it also becomes possible for signals to be communicated to individual sensors in a targeted manner. Such a pulse may be conducted for example via the m-th output line Al, with switches $P_A$ and $P_M$ activated, to the field-effect transistor of the measuring cell which serves as a sensor.

Figure 13:
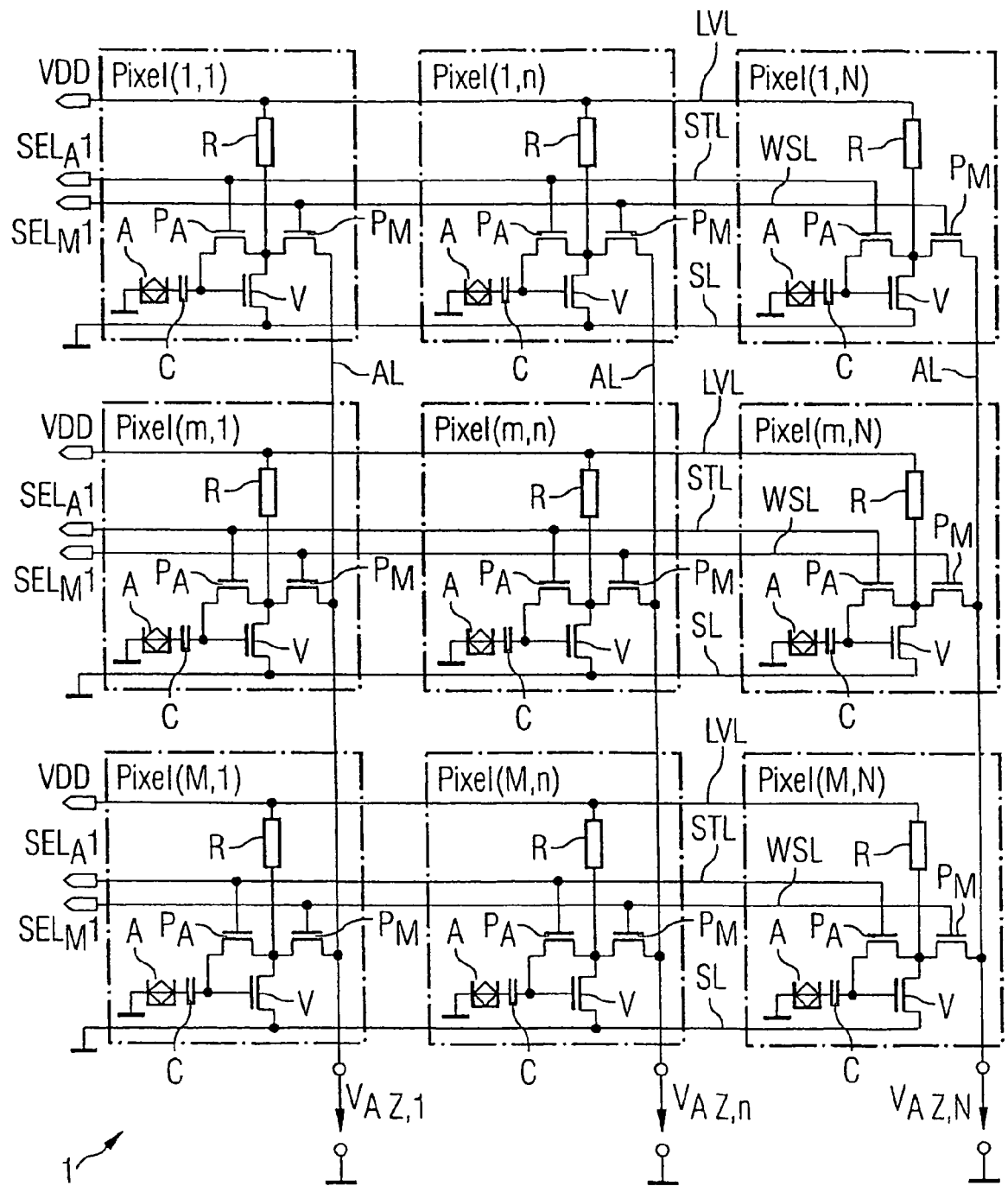
FIG. 13 shows a second electrical circuit diagram of a measuring array according to the invention.

FIG. 13 shows a measuring array having 3×3 measuring cells, also designated by the term "pixel" in the figure. The measuring cells 3 used correspond to the measuring cell construction according to FIG. 7.

Ground potential and respectively first supply potential $V_{DD}$ are applied to the load elements R and the source terminals via the horizontal—and thus pixel-row-connecting—source connecting lines SL and load-side connecting lines LVL. The potential difference between these potentials, which may also differ from the operating voltage of the chip, is thus dropped across the series circuit of the resistor R and the transistor V.

The switches $P_A$ of a pixel row are connected to one another via common control lines STL for each pixel row. The further switches $P_M$ of a pixel row are connected to one another via common further control lines WSL for each pixel row.

The further switches $P_M$ of each column are connected to one another via vertically running output lines AL.

For the method of operation, reference is made to the explanations with regard to the measuring array according to FIG. 12. In contrast thereto, however, the pixels can be read row by row in the case of the measuring array according to FIG. 13.

Figure 14:
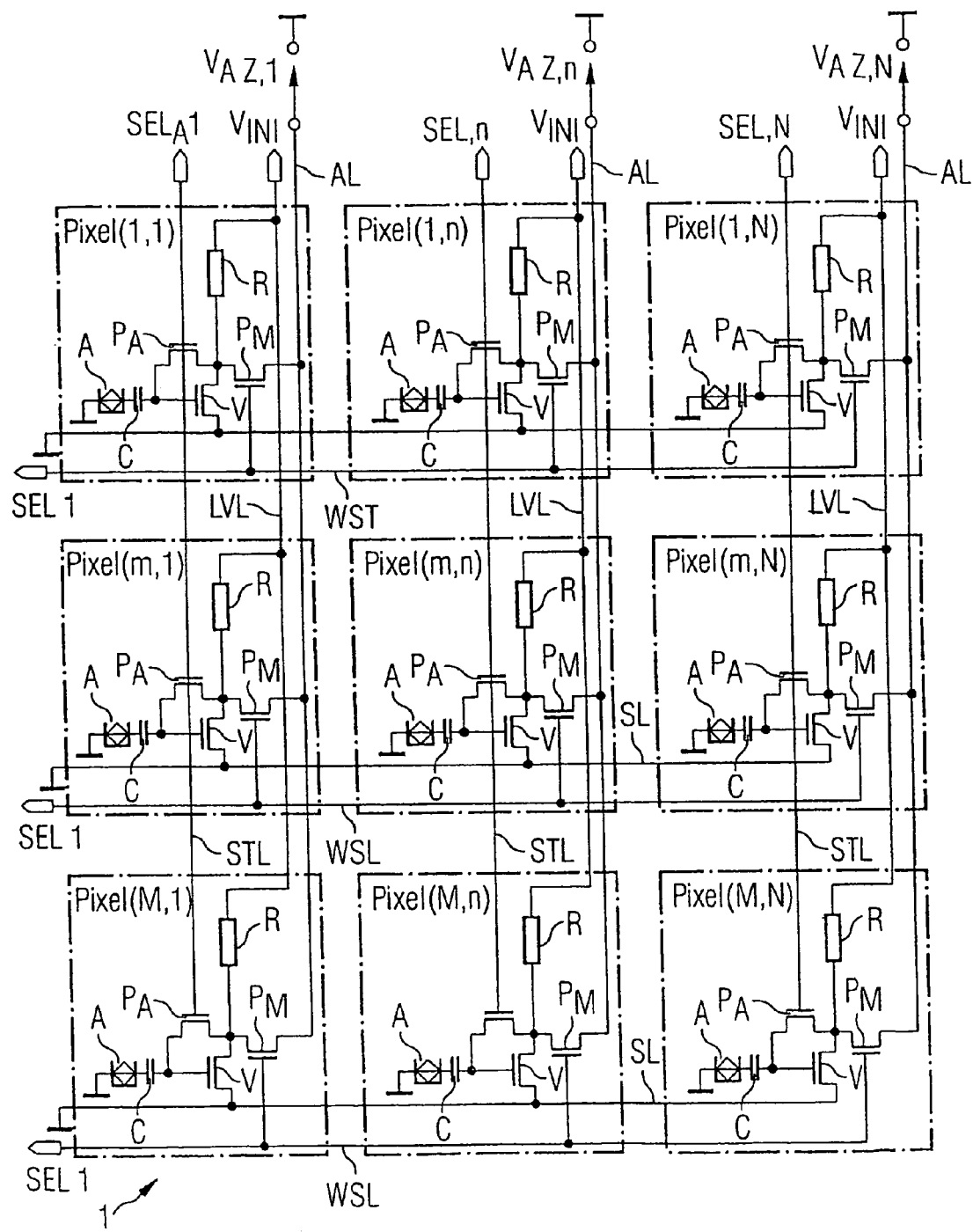
FIG. 14 shows a third electrical circuit diagram of a measuring array according to the invention.

FIG. 14 shows a measuring array having 3×3 measuring cells, also designated by the term "pixel" in the figure. The measuring cells 3 used correspond to the measuring cell construction according to FIG. 4.

Ground potential and respectively first supply potential $V_{DD}$ are applied to the load elements R and the source terminals via the horizontal—and thus pixel-row-connecting—source connecting lines SL and the vertical—and thus pixel-column-connecting—load-side connecting lines LVL. The potential difference between these potentials, which may also differ from the operating voltage of the chip, is thus dropped across the series circuit of the resistor R and the transistor V.

The switches $P_A$ of a pixel column are connected to one another via common control lines STL for each pixel column. The further switches $P_M$ of a pixel row are connected to one another via common further control lines WSL for each pixel row.

The further switches $P_M$ of each column are connected to one another via vertically running output lines AL.

With regard to the method of operation, reference is made to the explanations regarding the measuring array according to FIG. 12. The pixels will be read row by row in the case of the measuring array according to FIG. 14.

Figure 15:
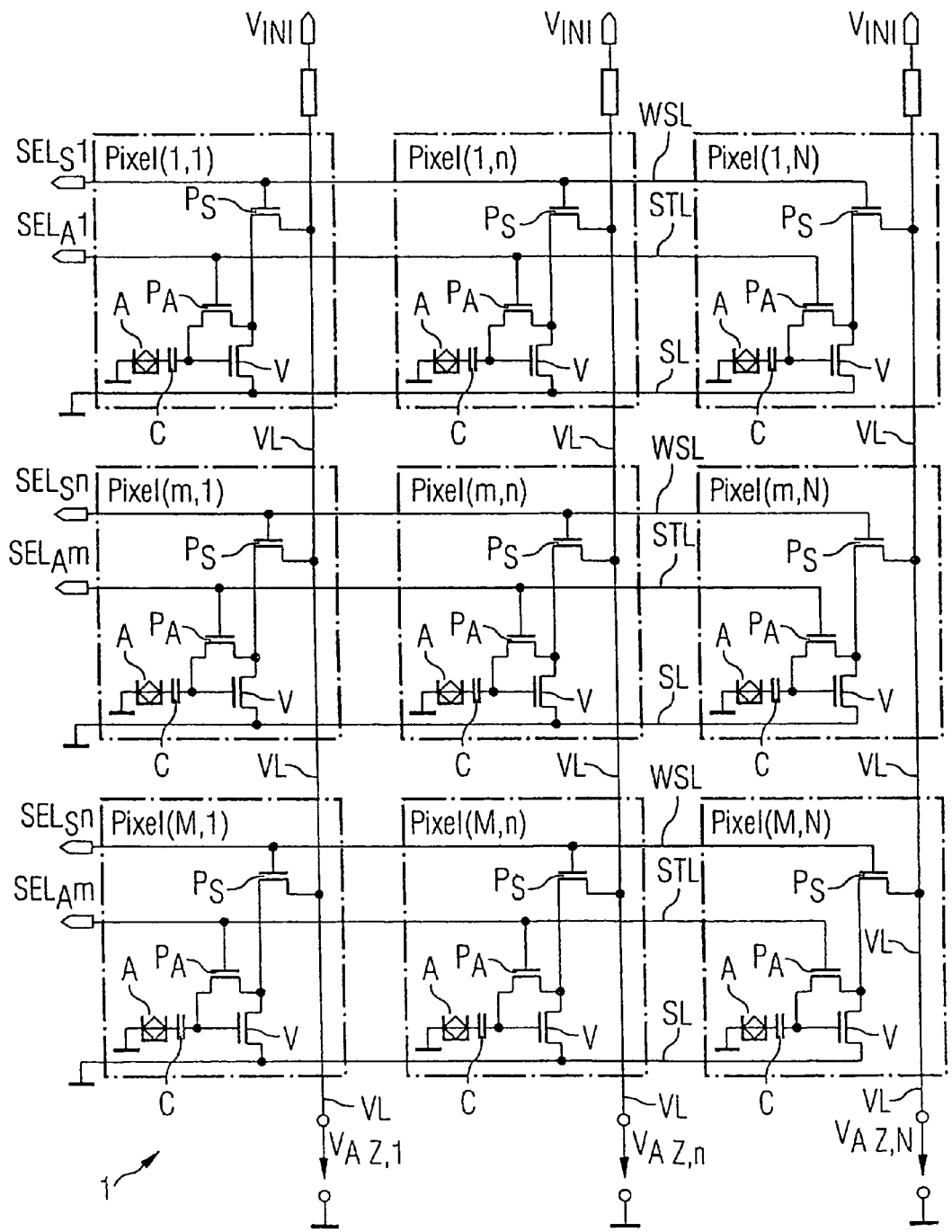
FIG. 15 shows a fourth electrical circuit diagram of a measuring array according to the invention.

FIG. 15 shows a measuring array having 3×3 measuring cells, also designated by the term "pixel" in the figure. The measuring cells 3 used correspond to the measuring cell construction according to FIG. 6.

Ground potential is applied to the source terminals via the horizontal—and thus pixel-row-connecting—source connecting lines SL. For each pixel column, now only one resistor arranged outside the substrate is provided as load element R.

Said load element R is connected to the first supply potential $V_{DD}$. The further switches $P_S$ of a pixel column are connected via a connecting line VL to the load element R assigned to this column, on the one hand, and to a tap for the output signal $V_A$, on the other hand.

The switches $P_A$ of a pixel row are connected to one another via common control lines STL for each pixel row. The further switches $P_S$ of a pixel row are connected to one another via common further control lines WSL for each pixel row.

Except for those further switches $P_S$ of the row to be read, all the further switches $P_S$ are driven with a low level and thus turned off. The further switches $P_S$ which are activated with a high level exhibit ohmic behavior or operate in the triode region. The transistors V—having the transconductance $g_m$ and the output conductance $g_d$—together with the resistors R and the activated further switches $P_S$—having the output conductance $g_{dPs}$—designed as switching transistors thus form an amplifier with the amplification of the gate voltage $V_G$ at the output $V_A$ by the factor $A_0$:

$$A_0 = \frac{\Delta V_A}{\Delta V_G} = R_1 \cdot g_m \cdot \frac{1}{1 + g_d \cdot \left(R_1 + \frac{1}{g_{dP_s}}\right)}. \quad (9)$$

In the case of the measuring array according to FIG. 15, the pixels are read row by row via the current-free part of the connecting line VL.

Figure 16:
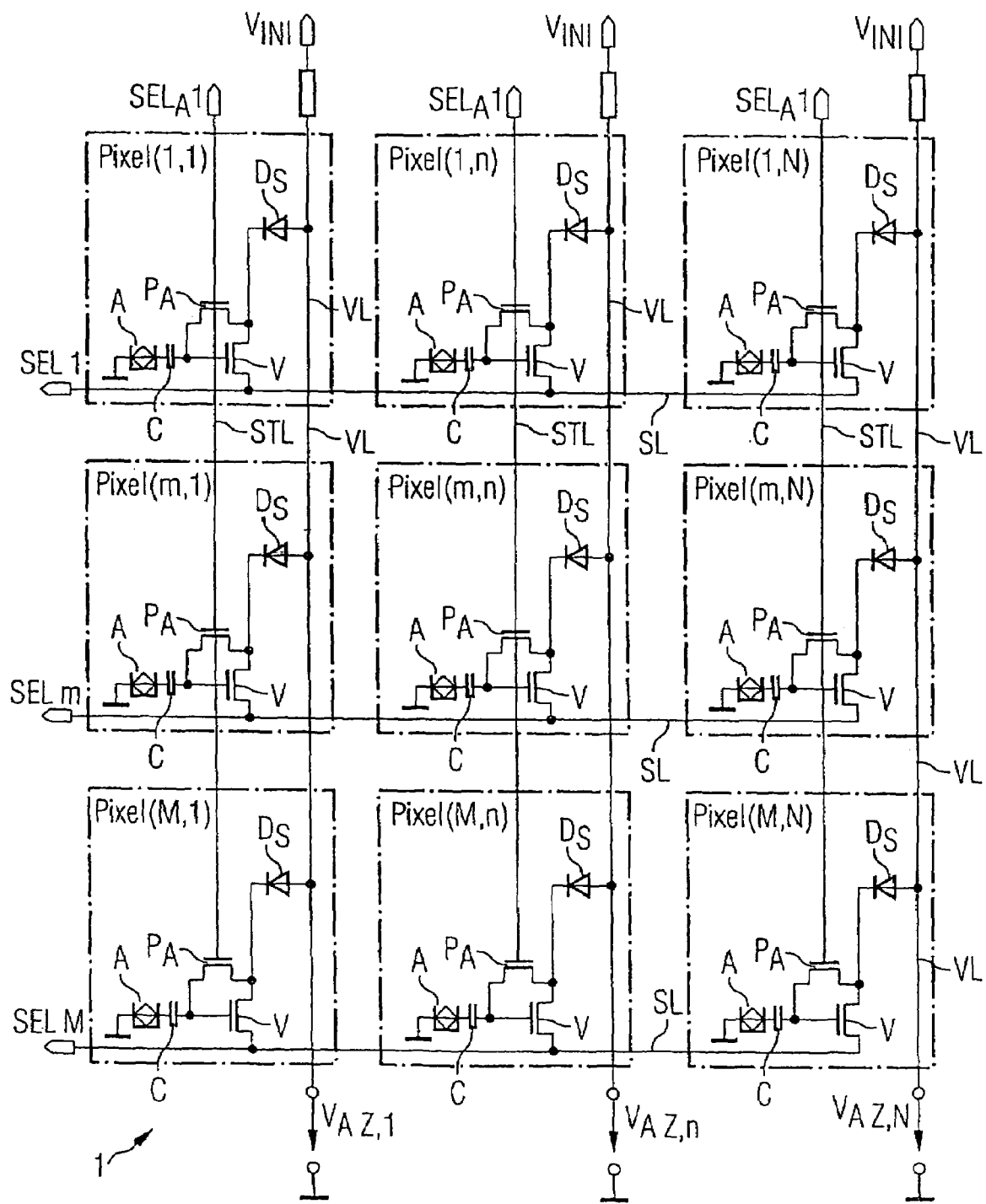
FIG. 16 shows a fifth electrical circuit diagram of a measuring array according to the invention.

FIG. 16 shows a measuring array having 3×3 measuring cells, also designated by the term "pixel" in the figure. The measuring cells 3 used essentially correspond to the measuring cell construction according to FIG. 6.

Ground potential is applied to the source terminals via the horizontal—and thus pixel-row-connecting—source connecting lines SL. For each pixel column, only one resistor arranged outside the substrate is provided as load element R. Said load element R is connected to the first supply potential $V_{DD}$. The further switches $P_M$ from FIG. 6 are replaced by a diode. The diodes $D_S$ of a pixel column are connected via a connecting line VL to the load element R assigned to this column, on the one hand, and to a tap for the output signal $V_A$, on the other hand.

The switches $P_A$ of a pixel column are connected to one another via common control lines STL for each pixel row.

Driving or selection of a row of measuring cells is preferably enabled by the connecting line SL of the driven row being put at ground potential and all the other horizontal connecting lines SL being put at the positive supply potential $V_{DD}$. The diodes $D_S$ in the measuring cells that are not driven then turn off since the diodes $D_S$ in these rows are reverse-biased. The diodes situated in the driven column are forward-biased and thus represent a small resistance which is negligible in comparison with the resistance of the load element R.

The pixels are thus read row by row in the case of the measuring array according to FIG. 16.

In an alternative advantageous embodiment variant, the measuring array can also be read column by column.

Figure 17:
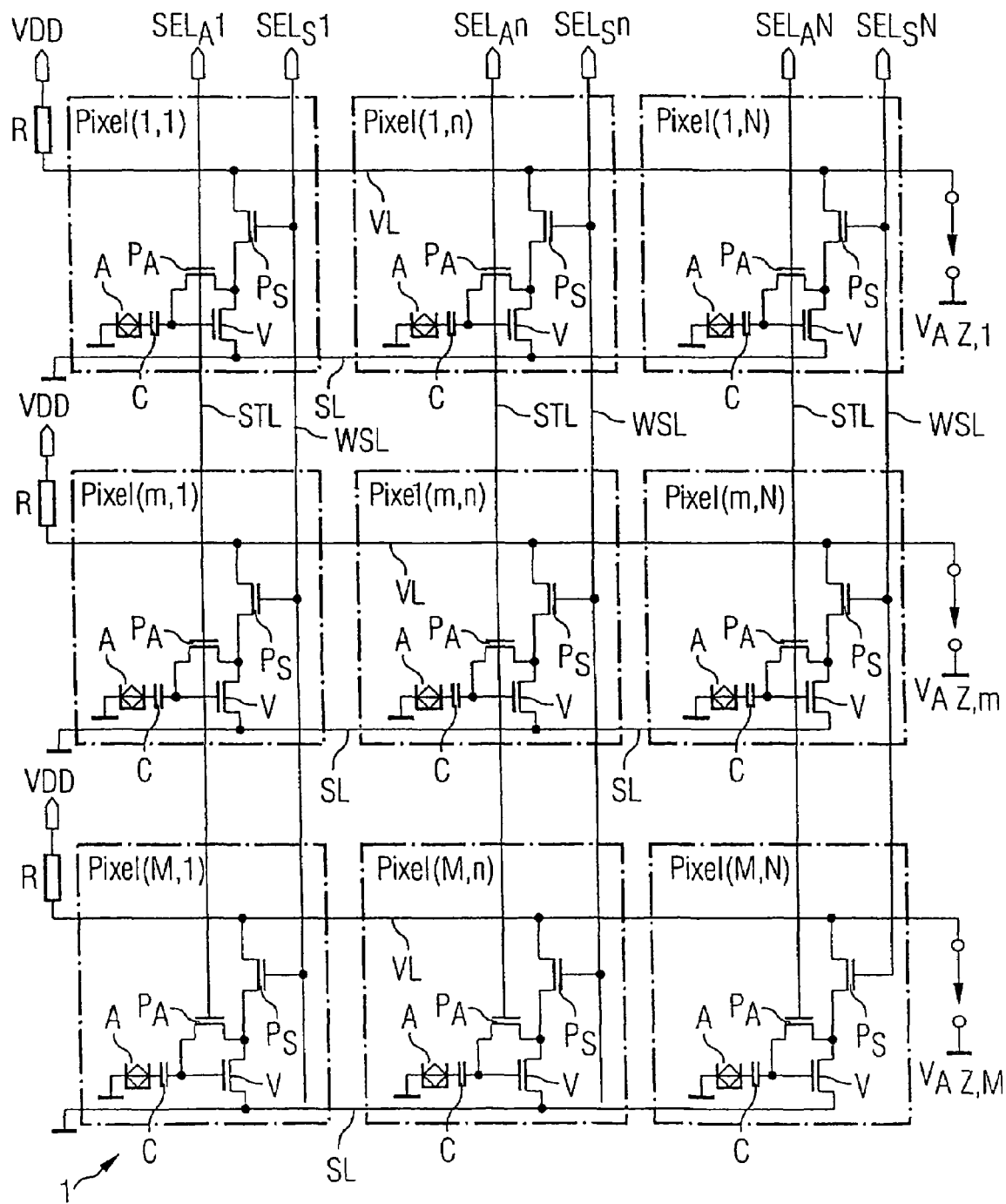
FIG. 17 shows a sixth electrical circuit diagram of a measuring array according to the invention.

FIG. 17 shows a measuring array having 3×3 measuring cells, also designated by the term "pixel" in the figure. The measuring cells 3 used correspond to the measuring cell construction according to FIG. 9.

Ground potential is applied to the source terminals via the horizontal—and thus pixel-row-connecting—source connecting lines SL. For each pixel row, now only one resistor arranged outside the substrate is provided as load element R. Said load element R is connected to the first supply potential $V_{DD}$. The further switches $P_M$ of a pixel row are connected via a connecting line VL to the load element R assigned to this column, on the one hand, and to a tap for the output signal $V_A$, on the other hand.

The switches $P_A$ of a pixel column are connected to one another via common control lines STL for each pixel column. The further switches $P_M$ of a pixel column are connected to one another via common further control lines WSL for each pixel column.

With regard to the method of operation, reference is made to the explanations regarding the measuring array according to FIG. 12. The pixels are read column by column in the case of the measuring array according to FIG. 17.

FIG. 18 shows a measuring array 1 in plan view. The views shown below the plan view are sections along the section lines S1–S1' and S2–S2' from the plan view.

In this case, the measuring cells 3 form the bottom of a well 6. The well 6 receives the sample 4/analyte during measuring operation. The sample can thus act on the sensors A of the measuring cells 3. Furthermore, the substrate 2 can be seen, which carries the measuring cells 3 and, in the present exemplary embodiment, is a silicon chip which carries the sensors and amplifier circuits constructed using CMOS technology.

In this case, the individual sensors may either be constructed identically and measure electrical potentials of the sample in a spatially resolved manner. Alternatively, the sensors may be constructed differently in order to measure different parameters/substances of the sample.

FIG. 19 shows a further measuring array in plan view and, below the latter, two sectional views along the section lines S1–S1' and S2–S2' from the plan view. In this case, a well does not receive the sample, rather a channel 5 guides the sample past the individual sensors A of the measuring cells 3 in the context of fluidics.

Here, too, the individual sensors may either be constructed identically and measure electrical potentials of the sample in a spatially resolved manner. Alternatively, the sensors may be constructed differently in order to measure different parameters/substances of the sample.

The invention claimed is:

1. A measuring cell for recording an electrical potential of an analyte situated on the measuring cell, comprising:
    a sensor being electrically insulated from the analyte; and
    an amplifier circuit connected to the sensor on a substrate and having an input stage containing a field-effect transistor or a bipolar transistor, the sensor being at least indirectly connected to a control terminal of the field-effect transistor or of the bipolar transistor,
    wherein an operating point of the amplifier circuit is set by means of a voltage or a current applied at the control terminal of the field-effect transistor or of the bipolar transistor of the input stage of the amplifier circuit.

2. The measuring cell as claimed in claim 1, wherein the amplifier circuit is configured in single-stage fashion.

3. The measuring cell as claimed in claim 1, wherein the amplifier circuit is configured in multi-stage fashion.

4. The measuring cell as claimed in claim 1, wherein the amplifier circuit has a feedback via which the voltage or the current is applied at the input stage of the amplifier circuit.

5. The measuring cell as claimed in claim 4, wherein the feedback is one of a first controllable switch, a low-pass filter, and a unit for externally storing an operating voltage.

6. The measuring cell as claimed in claim 1, further comprising:
a first load element provided to set the operating point of the field-effect transistor or of the bipolar transistor; and
a controllable switch connecting the control terminal of the field-effect transistor or of the bipolar transistor to the drain or the collector of the transistor, wherein the drain or the collector of the transistor is connected to a first supply potential via the first load element.

7. The measuring cell as claimed in claim 1, wherein the transistor is a field-effect transistor operated in a common-source connection.

8. The measuring cell as claimed in claim 1, wherein the transistor is a bipolar transistor operated in a common-emitter connection.

9. The measuring cell as claimed in claim 1, wherein the transistor contains subtransistors connected in a Darlington circuit.

10. The measuring cell as claimed in claim 6, wherein the first load element is a nonreactive resistor.

11. The measuring cell as claimed in claim 6, wherein the first load element is a transistor.

12. The measuring cell as claimed in claim 6, wherein the load of the first load element is adjustable.

13. The measuring cell as claimed in 6, wherein the first load element is arranged on the substrate.

14. The measuring cell as claimed in claim 6, wherein the first load element is arranged outside the substrate.

15. The measuring cell as claimed in claim 5, wherein the first controllable switch is a transistor.

16. The measuring cell as claimed in claim 5, wherein the first controllable switch is arranged on the substrate.

17. The measuring cell as claimed in claim 5, further comprising:
a measuring operating phase for measuring a potential of a sample, during which the first controllable switch is opened; and
a setting operating phase for setting the operating point of the amplifier circuit, during which the first controllable switch is closed.

18. The measuring cell as claimed in claim 5, further comprising a first load element connecting the control terminal of the transistor to the drain or the collector of the transistor.

19. The measuring cell as claimed in claim 5, further comprising:
a first load element connecting the control terminal of the transistor to the first supply potential; and
a second load element connecting the control terminal of the transistor to a second supply potential.

20. The measuring cell as claimed in claim 19, wherein the first load element and/or the second load element are arranged on the substrate.

21. The measuring cell as claimed in claim 1, wherein the substrate at least has terminals for a first supply potential, a second supply potential, and an electrical output signal.

22. The measuring cell as claimed in claim 5, wherein a second controllable switch is connected to the drain or the collector of the transistor.

23. The measuring cell as claimed in claim 18, wherein a second controllable switch is arranged between the drain or the collector of the transistor and the load element.

24. The measuring cell as claimed in claim 22, wherein the second controllable switch is arranged on the substrate.

25. The measuring cell as claimed in claim 1, wherein the sensor contains a field-effect transistor having gate, source and drain, and the sample is arranged above the gate during a measuring operation and the gate electrical potential is coupled to a channel current of the field-effect transistor between the source and the drain.

26. The measuring cell as claimed in claim 1, wherein the sensor contains a pH-sensitive layer.

27. The measuring cell as claimed in claim 1, wherein the sensor contains a substance-selective membrane.

28. A measuring array having a plurality of measuring cells as claimed in claim 1 provided on the substrate.

29. The measuring array as claimed in claim 28, wherein the plurality of measuring cells are arranged in rows and columns on the substrate.

30. The measuring array as claimed in claim 29, wherein the substrate includes a common source connecting line for connecting the source or the emitter terminals of one of either the cell rows or the cell columns.

31. The measuring array as claimed in claim 30, further comprising a common source connecting line provided for each of the cell rows or the cell columns, wherein the substrate includes a terminal for each of the common source connecting lines.

32. The measuring array as claimed in claim 29, wherein the substrate includes a common control line for controlling switches of one of either the cell columns or the cell rows.

33. The measuring array as claimed in claim 32, further comprising a common control line provided for each of the cell columns or the cell rows, wherein the substrate includes a terminal for each of the common control lines.

34. The measuring array as claimed in claim 30, wherein the substrate includes a plurality of first common control lines for controlling switches either of the respective cell rows or of the respective cell columns.

35. The measuring array as claimed in claim 34, further comprising a second common control line provided for each of the cell rows or the cell columns, wherein the substrate includes a terminal for each of the second common control lines.

36. The measuring array as claimed in claim 30, wherein the substrate includes a common load-side supply line for connecting load elements of one of either the cell columns or the cell rows.

37. The measuring array as claimed in claim 36, further comprising a common load-side supply line provided for each of the cell columns or the cell rows, wherein the substrate includes a terminal for each of the load-side supply lines.

38. The measuring array as claimed in claim 30, further comprising a diode connected to the drain or the collector of the transistor in each of the measuring cells, wherein the substrate contains a common connecting line for connecting all the diodes of one of either the cell columns or of the cell rows.

39. The measuring array as claimed in claim 38, further comprising:
- a common connecting line in each of the cell columns or the cell rows, wherein the substrate includes a first terminal for each of the connecting lines; and
- a load element arranged outside the substrate for each of the cell columns or for each of the cell rows, wherein each of the load elements is connected to the terminal of a respective one of the common connecting lines,
- wherein the substrate includes a second terminal for tapping off an electrical output signal for each of the common connecting lines.

40. The measuring array as claimed in claim 28, wherein the sensors of at least two different measuring cells are designed for detecting different parameters or substances of the sample.

41. The measuring array as claimed in claim 28, wherein the measuring cells form the bottom of a well which receives the sample during measuring operation.

42. The measuring array as claimed in claim 28, having a channel above the measuring cells for receiving the sample during measuring operation.

43. The use of a measuring cell as claimed in claim 1 for applying an electrical potential to a sample by the application of an electrical signal to the amplifier circuit.

44. The use of a measuring array as claimed in claim 28 for applying electrical potentials to a sample in a spatially resolved manner by the application of electrical signals to the amplifier circuits of the individual measuring cells.

45. A measuring array having a plurality of measuring cells as claimed in claim 22 provided on the substrate, wherein the plurality of measuring cells are arranged in rows and columns on the substrate, and wherein the substrate includes a common source connecting line for connecting the source or the emitter terminals of one of either the cell rows or the cell columns.

46. The measuring array as claimed in claim 45, wherein the substrate includes a common output line for connecting the second controllable switches of one of either the cell columns or of the cell rows.

47. The measuring array as claimed in claim 46, further comprising a common output line provided for each of the cell columns or the cell rows, wherein the substrate includes a terminal for each of the output lines.

48. A measuring array having a plurality of measuring cells as claimed in claim 23 provided on the substrate, wherein the plurality of measuring cells are arranged in rows and columns on the substrate, and wherein the substrate includes a common source connecting line for connecting the source or the emitter terminals of one of either the cell rows or the cell columns.

49. The measuring array as claimed in claim 48, wherein the substrate contains a common connecting line for connecting the second controllable switches of one of either the cell columns or of the cell rows.

50. The measuring array as claimed in claim 49, further comprising a common connecting line provided for each of the cell columns or the cell rows, wherein the substrate includes a first terminal for each of the connecting lines, and a load element is arranged outside the substrate for each of the cell columns or for each of the cell rows and is connected to the terminal of the respective common connecting line, and wherein the substrate includes a further terminal for tapping off an electrical output signal for each of the common connecting lines.

* * * * *